(12) United States Patent
Garcia-Bengochea et al.

(10) Patent No.: US 10,687,830 B2
(45) Date of Patent: Jun. 23, 2020

(54) METHODS AND DEVICES FOR SURGICAL ACCESS

(71) Applicant: Javier Garcia-Bengochea, Jacksonville, FL (US)

(72) Inventors: Javier Garcia-Bengochea, Jacksonville, FL (US); Marc Von Amsberg, Waxhaw, NC (US); Ryan Lewis, Cincinnati, OH (US)

(73) Assignee: Javier Garcia-Bengochea, Jacksonville, FL (US)

( * ) Notice: Subject to any disclaimer, the term of this patent is extended or adjusted under 35 U.S.C. 154(b) by 0 days.

(21) Appl. No.: 15/747,935

(22) PCT Filed: Jul. 26, 2016

(86) PCT No.: PCT/US2016/044119
§ 371 (c)(1),
(2) Date: Jan. 26, 2018

(87) PCT Pub. No.: WO2017/008087
PCT Pub. Date: Jan. 12, 2017

(65) Prior Publication Data
US 2018/0368861 A1 Dec. 27, 2018

Related U.S. Application Data

(63) Continuation-in-part of application No. 14/791,881, filed on Jul. 6, 2015, now Pat. No. 10,045,768.

(30) Foreign Application Priority Data

Jul. 6, 2015 (WO) .................. PCT/US2015/03920

(51) Int. Cl.
*A61B 17/17* (2006.01)
*A61F 2/46* (2006.01)
(Continued)

(52) U.S. Cl.
CPC ........ *A61B 17/1757* (2013.01); *A61B 17/025* (2013.01); *A61B 17/3209* (2013.01);
(Continued)

(58) Field of Classification Search
CPC ................ A61B 90/50; A61B 17/3209; A61B 2090/3966; A61B 2017/320052; A61B 90/11; A61F 2002/4687
See application file for complete search history.

(56) References Cited

U.S. PATENT DOCUMENTS 4,982,729 A 1/1991 Wu
5,020,519 A 6/1991 Hayes et al.
(Continued)

FOREIGN PATENT DOCUMENTS

RU 2005100288 A 6/2006
RU 2288650 C2 12/2006

OTHER PUBLICATIONS

Kamran Aghayev, Frank D. Vrionis, Mini-open lateral retroperitoneal lumbar spine approach using psoas muscle retraction technique. Technical report and initial results on six patients. Eur Spine J (2013), Ideas and Technical Innovations, Aug. 1, 2013, 22:2113-2119. Springer-Verlag Berlin Heidelberg 2013.

*Primary Examiner* — Ellen C Hammond
*Assistant Examiner* — Tara Rose E Carter
(74) *Attorney, Agent, or Firm* — McNees Wallace & Nurick LLC

(57) ABSTRACT

A surgical instrument assembly includes a frame system, and a surgical tool engageable with the frame system. The frame system is adapted for providing a surgical tool attachment and articulation locus that is maintained during the course of a surgical procedure to direct a fixed and repeatable delivery path for introduction and manipulation of one or more surgical instruments and implants at a surgical site in or on
(Continued)

the patient's anatomy. The delivery path can be substantially curvilinear along an arc that is defined by a radius of curvature and length defined by the surgical tool, and a predetermined range of articulation of the tool at the articulation locus.

20 Claims, 18 Drawing Sheets

Related U.S. Application Data

(60) Provisional application No. 62/197,093, filed on Jul. 26, 2015, provisional application No. 62/246,566, filed on Oct. 26, 2015.

(51) Int. Cl.
    *A61B 90/11*     (2016.01)
    *A61B 17/02*     (2006.01)
    *A61B 17/3209*     (2006.01)
    *A61B 17/00*     (2006.01)
    *A61B 90/00*     (2016.01)
    *A61B 17/32*     (2006.01)
    *A61B 90/50*     (2016.01)
(52) U.S. Cl.
    CPC .............. *A61B 90/11* (2016.02); *A61B 90/50* (2016.02); *A61F 2/4611* (2013.01); *A61B 2017/00261* (2013.01); *A61B 2017/0256* (2013.01); *A61B 2017/320052* (2013.01); *A61B 2090/3966* (2016.02); *A61F 2002/4681* (2013.01); *A61F 2002/4687* (2013.01)

(56) References Cited

U.S. PATENT DOCUMENTS

| | | | |
|---|---|---|---|
| 5,056,523 A * | 10/1991 | Hotchkiss, Jr. | A61B 17/3403 378/37 |
| 5,489,307 A | 2/1996 | Kuslich et al. | |
| 5,499,964 A | 3/1996 | Beck et al. | |
| 5,522,899 A | 6/1996 | Michelson | |
| 5,562,736 A | 10/1996 | Ray et al. | |
| 5,772,583 A * | 6/1998 | Wright | A61B 17/0206 403/389 |
| 5,792,044 A | 8/1998 | Foley et al. | |
| 5,795,291 A | 8/1998 | Koros et al. | |
| 5,799,055 A | 8/1998 | Peshkin et al. | |
| 5,888,197 A | 3/1999 | Mulac et al. | |
| 5,902,233 A | 5/1999 | Farley et al. | |
| 5,908,382 A * | 6/1999 | Koros | A61B 17/0206 600/215 |
| 5,928,139 A | 7/1999 | Koros et al. | |
| 5,944,658 A | 8/1999 | Koros et al. | |
| 5,976,146 A | 11/1999 | Ogawa et al. | |
| 5,980,504 A | 11/1999 | Sharkey et al. | |
| 6,017,008 A | 1/2000 | Farley | |
| 6,159,215 A | 12/2000 | Urbahns et al. | |
| 6,187,000 B1 | 2/2001 | Davison et al. | |
| 6,224,595 B1 | 5/2001 | Michelson | |
| 6,224,607 B1 | 5/2001 | Michelson | |
| 6,235,028 B1 | 5/2001 | Brumfield et al. | |
| 6,287,313 B1 | 9/2001 | Sasso | |
| 6,319,257 B1 | 11/2001 | Carignan et al. | |
| 6,371,968 B1 | 4/2002 | Kogasaka et al. | |
| 6,419,678 B1 | 7/2002 | Asfora | |
| 6,436,098 B1 | 8/2002 | Michelson | |
| 6,447,512 B1 | 9/2002 | Landry et al. | |
| 6,491,694 B1 * | 12/2002 | Orsak | A61B 17/6425 606/57 |
| 6,500,180 B1 | 12/2002 | Foley et al. | |
| 6,511,423 B2 | 1/2003 | Farley | |
| 6,520,907 B1 | 2/2003 | Foley et al. | |
| 6,524,312 B2 | 2/2003 | Landry et al. | |
| 6,524,318 B1 | 2/2003 | Longhini et al. | |
| 6,524,320 B2 | 2/2003 | DiPoto | |
| 6,530,926 B1 | 3/2003 | Davison | |
| 6,530,929 B1 | 3/2003 | Justis et al. | |
| 6,554,836 B2 | 4/2003 | Michelson | |
| 6,558,390 B2 | 5/2003 | Cragg | |
| 6,575,979 B1 | 6/2003 | Cragg | |
| 6,595,998 B2 | 7/2003 | Johnson et al. | |
| 6,663,637 B2 | 12/2003 | Dixon et al. | |
| 6,733,496 B2 | 5/2004 | Sharkey et al. | |
| 6,783,528 B2 | 8/2004 | Vincent-Prestigiacomo | |
| 6,849,064 B2 | 2/2005 | Hamada | |
| 6,851,430 B2 | 2/2005 | Tsou | |
| 6,855,148 B2 | 2/2005 | Foley et al. | |
| 6,896,680 B2 | 5/2005 | Michelson | |
| 6,997,929 B2 | 2/2006 | Manzi et al. | |
| 7,004,945 B2 | 2/2006 | Boyd et al. | |
| 7,008,431 B2 | 3/2006 | Simonson | |
| 7,118,579 B2 | 10/2006 | Michelson | |
| 7,179,225 B2 | 2/2007 | Shluzas et al. | |
| 7,207,991 B2 | 4/2007 | Michelson | |
| 7,226,451 B2 | 6/2007 | Shluzas et al. | |
| 7,232,411 B2 | 6/2007 | Dinkier, II et al. | |
| 7,291,149 B1 | 11/2007 | Michelson | |
| 7,326,203 B2 | 2/2008 | Papineau et al. | |
| 7,416,553 B2 | 8/2008 | Patel et al. | |
| 7,491,168 B2 | 2/2009 | Raymond et al. | |
| 7,691,120 B2 | 4/2010 | Shluzas et al. | |
| 7,713,281 B2 | 5/2010 | Leeflang et al. | |
| 7,766,930 B2 | 8/2010 | DiPoto et al. | |
| 7,776,047 B2 | 8/2010 | Fanger et al. | |
| 7,799,033 B2 | 9/2010 | Assell et al. | |
| 7,875,049 B2 | 1/2011 | Eversull et al. | |
| 7,909,829 B2 | 3/2011 | Patel et al. | |
| 7,909,848 B2 | 3/2011 | Patel et al. | |
| 7,951,153 B2 | 5/2011 | Abdou | |
| 7,981,029 B2 | 7/2011 | Branch et al. | |
| 7,993,350 B2 | 8/2011 | Ventura et al. | |
| 8,066,714 B2 | 11/2011 | Shipp et al. | |
| 8,100,828 B2 | 1/2012 | Frey et al. | |
| 8,114,088 B2 | 2/2012 | Miller | |
| 8,152,714 B2 | 4/2012 | Garcia-Bengochea et al. | |
| 8,206,292 B2 | 6/2012 | Eckman | |
| 8,206,449 B2 | 6/2012 | Jansen et al. | |
| 8,235,999 B2 | 8/2012 | Simonson | |
| 8,277,486 B2 | 10/2012 | Davison | |
| 8,292,896 B2 | 10/2012 | Abdou | |
| 8,303,601 B2 | 11/2012 | Bandeira et al. | |
| 8,343,163 B1 | 1/2013 | Arambula et al. | |
| 8,357,184 B2 | 1/2013 | Woolley et al. | |
| 8,361,151 B2 | 1/2013 | Simonson | |
| 8,376,942 B2 | 2/2013 | Krauter et al. | |
| 8,425,602 B2 | 4/2013 | Guyer et al. | |
| 8,425,610 B2 | 4/2013 | Guyer et al. | |
| 8,444,678 B2 | 5/2013 | Simonson et al. | |
| 8,449,463 B2 | 5/2013 | Nunley et al. | |
| 8,450,288 B2 | 5/2013 | Boyd | |
| 8,568,306 B2 | 10/2013 | Hardenbrook | |
| 8,673,013 B2 | 3/2014 | Abdou | |
| 8,728,162 B2 | 5/2014 | Akyuz et al. | |
| 8,808,305 B2 | 8/2014 | Kleiner | |
| 8,840,622 B1 | 9/2014 | Vellido et al. | |
| 8,864,770 B2 | 10/2014 | Blain et al. | |
| 8,876,904 B2 | 11/2014 | Pimenta et al. | |
| 8,882,661 B2 | 11/2014 | Hutton et al. | |
| 8,911,364 B2 | 12/2014 | Feigenwinter et al. | |
| 8,945,003 B2 | 2/2015 | Bass et al. | |
| 2002/0099269 A1 * | 7/2002 | Martin | A61B 17/0206 600/201 |
| 2003/0158463 A1 * | 8/2003 | Julian | A61B 17/00234 600/104 |
| 2003/0176772 A1 | 9/2003 | Yang | |
| 2003/0199885 A1 | 10/2003 | Davison et al. | |
| 2005/0165405 A1 | 7/2005 | Tsou | |
| 2005/0197623 A1 | 9/2005 | Leeflang et al. | |
| 2006/0089652 A1 | 4/2006 | Eckman | |
| 2006/0111728 A1 | 5/2006 | Abdou | |
| 2006/0229627 A1 | 10/2006 | Hunt et al. | |

(56) References Cited

U.S. PATENT DOCUMENTS

| | | |
|---|---|---|
| 2006/0229636 A1 | 10/2006 | Woodburn et al. |
| 2006/0264960 A1 | 11/2006 | Kuslich et al. |
| 2006/0293678 A1 | 12/2006 | Davison et al. |
| 2007/0213739 A1 | 9/2007 | Michelson |
| 2007/0260270 A1 | 11/2007 | Assell et al. |
| 2007/0270866 A1 | 11/2007 | von Jako |
| 2008/0108940 A1 | 5/2008 | Sharkey et al. |
| 2008/0221586 A1 | 9/2008 | Garcia-Bengochea et al. |
| 2009/0234399 A1 | 9/2009 | Cragg |
| 2009/0264941 A1 | 10/2009 | Banouskou |
| 2010/0076502 A1* | 3/2010 | Guyer .............. A61B 17/02 606/86 R |
| 2010/0137922 A1 | 6/2010 | Hunt et al. |
| 2010/0160985 A1 | 6/2010 | Pannu |
| 2010/0217088 A1 | 8/2010 | Heiges et al. |
| 2011/0034777 A1 | 2/2011 | Ames et al. |
| 2011/0125163 A1 | 5/2011 | Rutten et al. |
| 2011/0166611 A1 | 7/2011 | Stinson |
| 2011/0201897 A1 | 8/2011 | Bertagnoli et al. |
| 2011/0237898 A1 | 9/2011 | Stone et al. |
| 2012/0029635 A1 | 2/2012 | Schoenhoeffer et al. |
| 2012/0071980 A1 | 3/2012 | Purcell et al. |
| 2012/0083887 A1 | 4/2012 | Purcell et al. |
| 2012/0101506 A1 | 4/2012 | Shim et al. |
| 2012/0130161 A1 | 5/2012 | Lauryssen et al. |
| 2012/0215229 A1 | 8/2012 | Garcia-Bengochea et al. |
| 2012/0232350 A1 | 9/2012 | Seex |
| 2012/0259343 A1 | 10/2012 | Clark et al. |
| 2012/0265310 A1 | 10/2012 | Fabian |
| 2012/0271120 A1 | 10/2012 | Seex |
| 2012/0310048 A1 | 12/2012 | Siegal et al. |
| 2013/0225935 A1 | 8/2013 | Nunley et al. |
| 2014/0039267 A1 | 2/2014 | Seex et al. |
| 2014/0172029 A1 | 6/2014 | Guyer et al. |
| 2014/0194697 A1 | 7/2014 | Seex |
| 2014/0316212 A1 | 10/2014 | Reimels |
| 2014/0371540 A1 | 12/2014 | Hutton et al. |
| 2015/0250466 A1 | 9/2015 | Thornburg |
| 2016/0287236 A1 | 10/2016 | Garcia-Bengochea et al. |

* cited by examiner

METHODS AND DEVICES FOR SURGICAL ACCESS

PRIORITY CLAIM; RELATED APPLICATIONS

This application claims priority to and is a 35 USC 371 US National Stage application of International Patent Application No. PCT/US2016/044119 that was filed on Jul. 26, 2016, which has a priority date of Jul. 26, 2015, and which claims priority to U.S. Provisional Applications Ser. No. 62/197,093 filed Jul. 26, 2015, and 62/246,566 filed Oct. 26, 2015. This application is also a continuation in part of U.S. patent application Ser. No. 14/791,881 filed Jul. 6, 2015, now U.S. Pat. No. 10,045,768 issued on Aug. 14, 2018, and is related to the divisional U.S. patent application Ser. No. 16/028,817 filed Jul. 6, 2018, each of which claim the benefit under 35 U.S.C. § 119(e) to U.S. Provisional Application Ser. No. 62/021,202 filed Jul. 6, 2014, and Nos. 62/080,609, 62/080,573, 62/080,578, 62/080,590, 62/080,557, all filed Nov. 17, 2014, and No. 62/156,184, filed May 1, 2015, the entireties of which are incorporated herein by reference.

BACKGROUND

Field

The present application describes various exemplary devices, systems and surgical techniques for achieving access to a site within the body, particularly the spine. More particularly, the present application describes a system and device components useful for accessing the spine for one or more purposes of manipulation, removal, replacement and reinforcement of intervertebral discs, particularly in the lumbar spine.

Description of the Related Art

Delivery of spinal devices is typically achieved using a variety of instruments that penetrate, dilate, retract and distract soft and bony tissue. Often these systems involve the use of clamps frames and other systems for temporarily holding and fixing placement of instruments relative to the patient. And common to the use of many of the surgical instruments is manipulation of tissue by pounding or banging on handles and strike plates to drive motion of instruments or implants through or into the tissue, particularly for distracting bones and inserting implants into bones. There is need in the art for instrument delivery systems and devices that enable precise and repeatable targeting of instruments and implants to the tissue and that dissipate or dampen the concussive effects associated with clinical techniques, particularly those used in orthopedic and spinal surgery.

SUMMARY

In accordance with the disclosure, a surgical instrument assembly is provided that includes a frame system, and a surgical tool engageable with the frame system. The frame system is adapted for providing a surgical tool attachment and articulation locus that is maintained during the course of a surgical procedure to direct a fixed and repeatable delivery path for introduction and manipulation of one or more surgical instruments and implants into a surgical site in or on the patient's anatomy, the delivery path being substantially curvilinear along an arc that is defined by a radius of curvature of the surgical tool, a length of an attachment arm of the surgical tool to the support rod, and a predetermined range of articulation of the articulation locus.

In some embodiments, the present invention provides methods for performing a procedure on the spine of a patient utilizing the surgical systems hereof to enable controlled and reliable delivery of instruments and implants into the spine along a predetermined and controlled path.

Embodiments of the present invention are not limited to use in a posterior-lateral approach for spinal surgery, and in other orientations and other surgical sites within the body.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
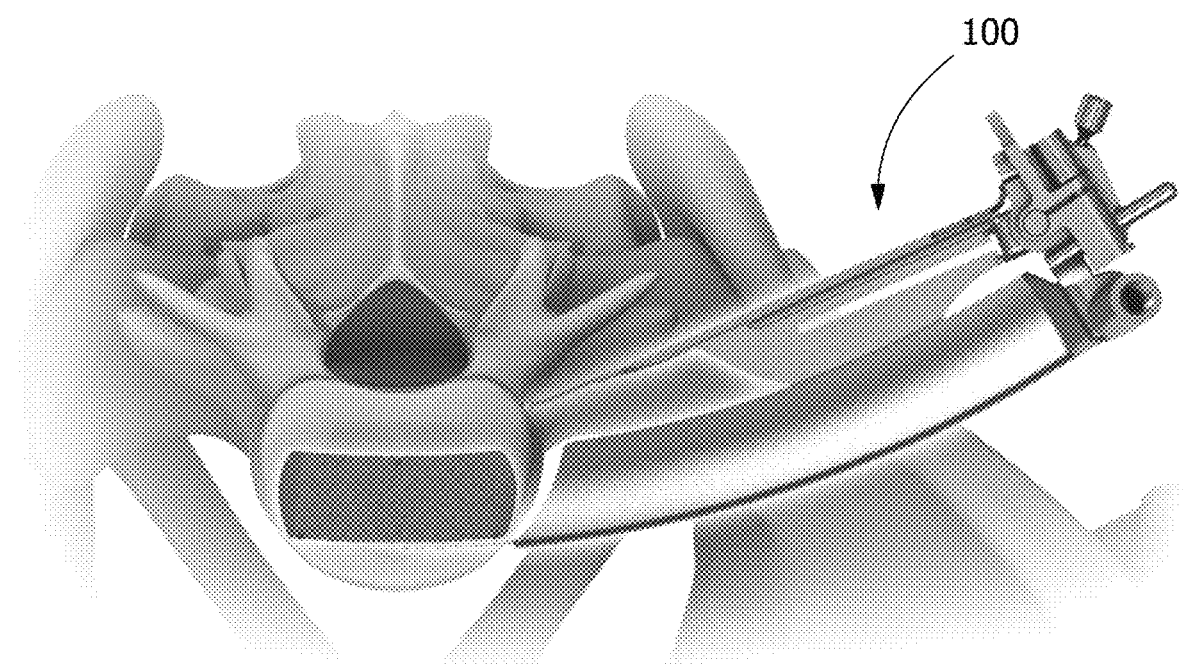
FIG. 1 is a schematic showing an assembled modular retractor in accordance with the disclosure in relation to a spine as seen along the inferior to superior axis.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise the terms "dorsal" and "posterior" indicate a direction toward the back, and the terms "ventral" and "anterior" indicate a direction toward the front. And the term "lateral" indicates a direction toward a side of the patient, the term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, according to some of the exemplary embodiments described herein, such references may be based on a representative spinal access modular retractor system having a radius of curvature as described, being suitable for any number of animal patients, including humans and other species. Of course, the type of surgery, target tissue, and species of patient may be different than is disclosed in the exemplary embodiments described herein, and in some embodiments, all or most components of the system may be rectilinear or combinations of rectilinear and curvilinear.

Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

There is a need for devices and systems that overcome the shortcomings in the art pertaining to surgical access, and in some particular instances, minimally invasive surgical access, particularly access for spinal surgery. In view of this need, the embodiments of devices, systems, and surgical methods provided herein address a variety of objects and advantages. The present application describes various exemplary devices, systems and surgical methods for achieving surgical access to a site within the body, particularly the spine. More particularly, the present application describes a system and device components for providing a system for positioning, securing and optimizing surgery with a minimally invasive modular retractor system for directly viewing and accessing a surgical site in the body, particularly the spine. In some exemplary embodiments, the system and device components are useful for accessing the spine for one or more purposes of neural decompression, manipulation, removal, and replacement and reinforcement of intervertebral discs, particularly in the lumbar spine.

Referring now to the drawings, FIG. 1 shows schematically an exemplary assembled modular retractor in accordance with the disclosure in relation to a spine as seen along the inferior to superior axis. More particularly, FIG. 1 shows positioned within the disc space a generally rectangular profile implant as placed through a modular retractor positioned on a lateral edge of the disc space.

In certain embodiments, the modular retractor system is suitable for facilitating placement of one or more implants to achieve interbody fusion between adjacent vertebrae, and in particular, lumbar interbody fusion. Referring to the representative embodiment of the modular retractor system shown in FIG. 1, the direct visualization modular retractor system enables creation of an open and essentially unobstructed channel for visualizing and surgically accessing the spine. As more fully described herein below and in the representative drawings, the modular retractor system includes, in various embodiments, features that enable stable positioning relative to the spine, and soft tissue-sparing retraction of nerves and muscle.

Advantageously, in certain embodiments, a curvilinear shape of the direct visualization modular retractor system 100, as depicted in FIG. 1, is particularly well suited for achieving lateral approach to the spine through a posterior access site. A key challenge in the field of spine surgery is delivery of anatomically matched implants into the disc space with minimal disruption of soft tissue and under surgical conditions that address surgeon and patient comfort and minimize surgical time and costs. The posterior-lateral procedure begins with placing a patient in a prone position on a surgical table (e.g., Jackson Table) with the axis of the lumbar spine generally parallel with the operating room floor. Posterior-lateral access and prone positioning of the patient offers many advantages over the current alternative approaches to lumbar interbody fusion, including, but not limited to: eliminating the need to reposition the patient for posterior stabilization and minimizing risk to vital soft tissues as compared with anterior lumbar interbody fusion; minimizing nerve compression compared to a straight oblique approach; delivering an implant with better anatomic physiology without requiring drastic repositioning; protecting anterior aspect and protecting the bowels from injury; preserving posterior bone; allowing use of a larger implant and avoidance of bone removal as compared with transforaminal lumbar interbody fusion; and presenting the patient in manner that is more familiar to the typical spine surgeon and more comfortable for the surgical subject as compared with the extreme lateral lumbar interbody fusion and other direct lateral lumbar interbody fusion procedures.

While various features and aspects of the modular retractor may vary according to the disclosure, in some embodiments of the instant invention, the modular retractor components are particularly suited for posterior-lateral access to the spine, wherein one or more components has a generally curved profile, being curved along an elongate axis. In yet other embodiments, the devices and systems are particularly suited for a surgical procedure that is achieved along a generally rectilinear (i.e., uncurving) path, such as via a direct anterior, posterior, or lateral approach wherein suitable embodiments of the device and system components are essentially rectilinear, or have a nominal curvature with a radius of curvature.

Of course, it will be appreciated that other modes of access to the spine can also be achieved, particularly with alternate retractor systems, and in particular, non-curvilinear embodiments of the modular retractor system, as described herein below. Likewise, it will be appreciated that any one or more of a variety of surgical procedures can be performed through various embodiments of a direct visualization modular retractor system, including but not limited to, removal of annulus material, vertebral distraction, graft and/or interbody implant insertion, and attachment of one or more plates and/or screws. In addition to enabling direct visualization for a lateral approach to the spine, other specific features and advantages of the modular retractor system and the surgical technique are described further herein. In particular, as provided herein, use of a modular retractor system with one or more of surgical guidance instruments and support frames allow enhanced precise targeting and control of surgical access that provide the benefits of improved options for implant placement and to reduction or elimination of the concussive effects on the clinician and the patient that are common with spinal surgery.

Surgical Guidance

In accordance with various embodiments, systems, techniques and instruments are provided that facilitate selection of incision site on the exterior of a patient's anatomy, selection of entry site on a target within the patient's anatomy, for example, entry into the disc space, and reliable positioning and path control for insertion of one or more instruments for accessing a target within a patient's anatomy.

In accordance with various embodiments herein, surgical guidance may be achieved using one or more frame systems together with one or more surgical tools or instruments, including but not limited to, trajectory guide arms, incision guidance instruments, tissue manipulation instruments, anatomically contoured implants, and combinations of these.

Support Frame

In various embodiments as depicted in the drawings a support frame 200 is provided which is attachable to a surgical table and is used for securing surgical instruments to stably position them during surgery and to enable dissipation of concussive force during soft and bony tissue procedures. The frame includes conventional surgical frame elements together with novel elements that enable concussive forces to be dissipated across the framework. In various embodiments, the framework is adapted with various clamps for affixing instruments to the rails and includes attachable bolsters that can be positioned adjacent to a patient's body parts to brace the body tissue and provide counter resistance during instrument manipulation.

Figure 2:
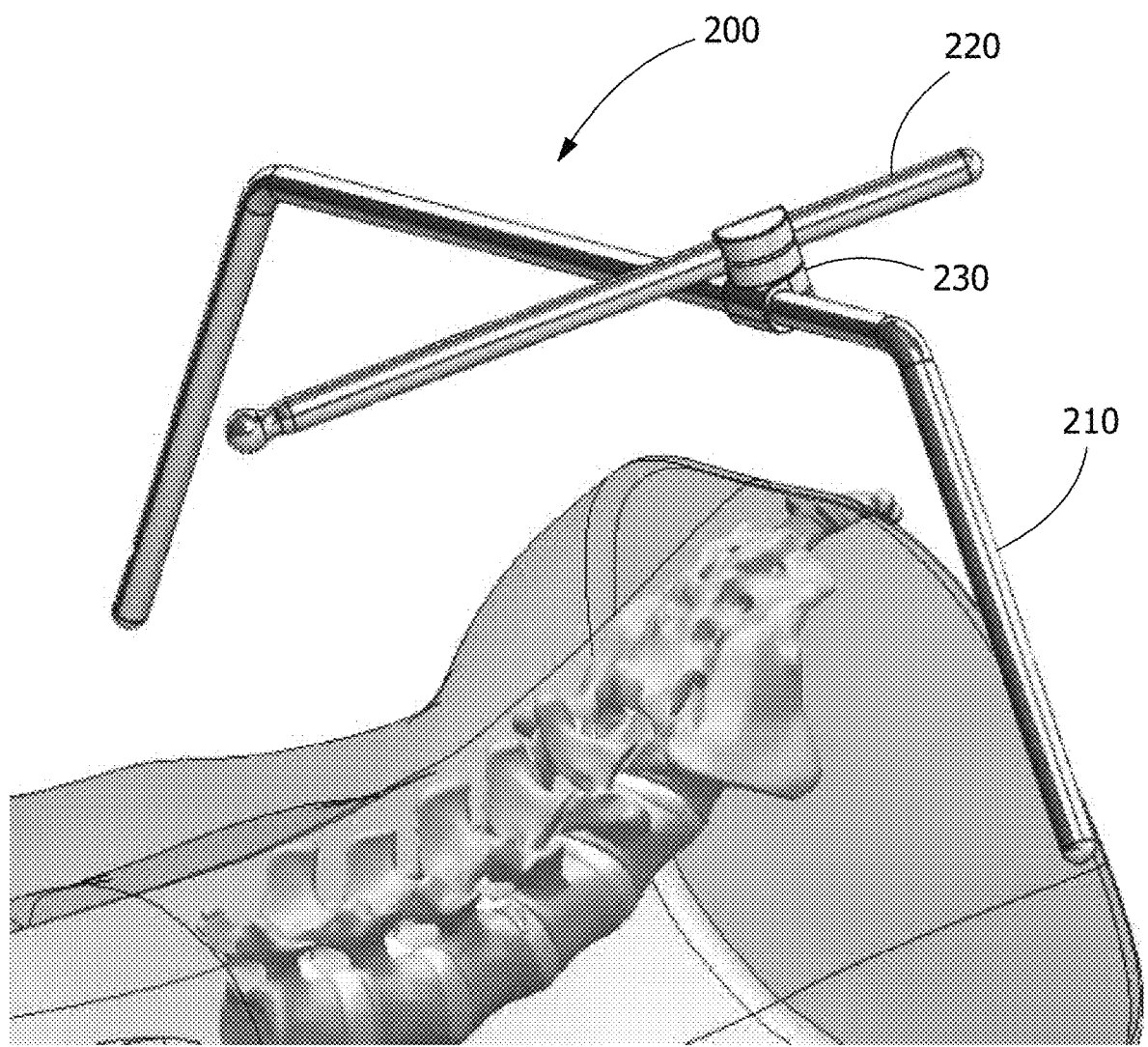
FIG. 2 is a schematic showing a portion of a lumbar spine in the context of a frame system according to the disclosure.

Referring now to FIGS. 2-7, and 10-17, various views of alternate embodiments of a frame 200 system are shown. Referring now to FIG. 2, in one example, a frame 200 may include at least one crossbar 210 that in some instances is oriented on the support surface such as a surgical table so that it runs generally perpendicular to the axis of a patient's spine when the patient is lying on the table, in some examples in a prone (or supine) position, the cross bar affixed to a frame that is fixedly mounted to the surgical table. Extending from the crossbar is a support bar 220 that can be positioned variably to generally align with the patient's spine providing an attachment locus for engaging with one or more instruments, for example, one or more positioning, surgical and modular retractor instruments, as further described herein. In a particular embedment, the support bar can be attached to the crossbar with an adjustable connector 230, such as a clamp, enabling adjustment in one, two, three or four planes.

In some embodiments, the attachment of the support bar to the crossbar allows adjustment in two planes, vertically and laterally. In yet other embodiments, attachment of the support bar to the crossbar may be a swivel type, that allows for multiple degrees of freedom, wherein the support bar is affixed to the cross bar with a clamp that allows rotational freedom around the axis of the crossbar, rotational freedom around the axis of the support bar, and rotational freedom around an axis that is perpendicular to the axis of the crossbar. Exemplary drawings of such a crossbar frame system are shown in FIGS. 2-7, and 10-17.

In accordance with various embodiments, the frame system and cross or parallel bars are used to support instruments for directing access to anatomical targets, such as the spine. Referring again to the drawings, for example, the embodiment of the invention as shown in FIGS. 2-4, the depicted support bar is suitable for attachment to a variety of instruments and guides, and has at a first end an attachment feature an adjustable pivot assembly 240 allowing multiple degrees of freedom for attachment a bar of the frame, as described above.

According to some embodiments, the support bar is configured at a second end with a generally spherical head 250 that is adapted to engage with instruments, the generally spherical head allowing for multiple degrees of freedom of engagement and attachment to instruments. Referring now to FIG. 7-FIG. 10, it will be appreciated that the spherical head is suitable for establishing a fixed spatial position of the fixation to a surgical instrument with very minimal constraint as to the spatial positioning of the cross or parallel frame bars and with very minimal constraint as to the spatial positioning of the support bar. As shown alternately in FIG. 6 and FIG. 8, respectively, the support bar may be either aligned with the patient's spine or may transect the patient's spine, yet in either case, the spherical head of the support bar is in the same point in space relative to the relevant spinal target, enabling great flexibility in the assembly of the frame and support system, while ensuring the proper selection of the rotational locus for instrument targeting.

Figure 3:
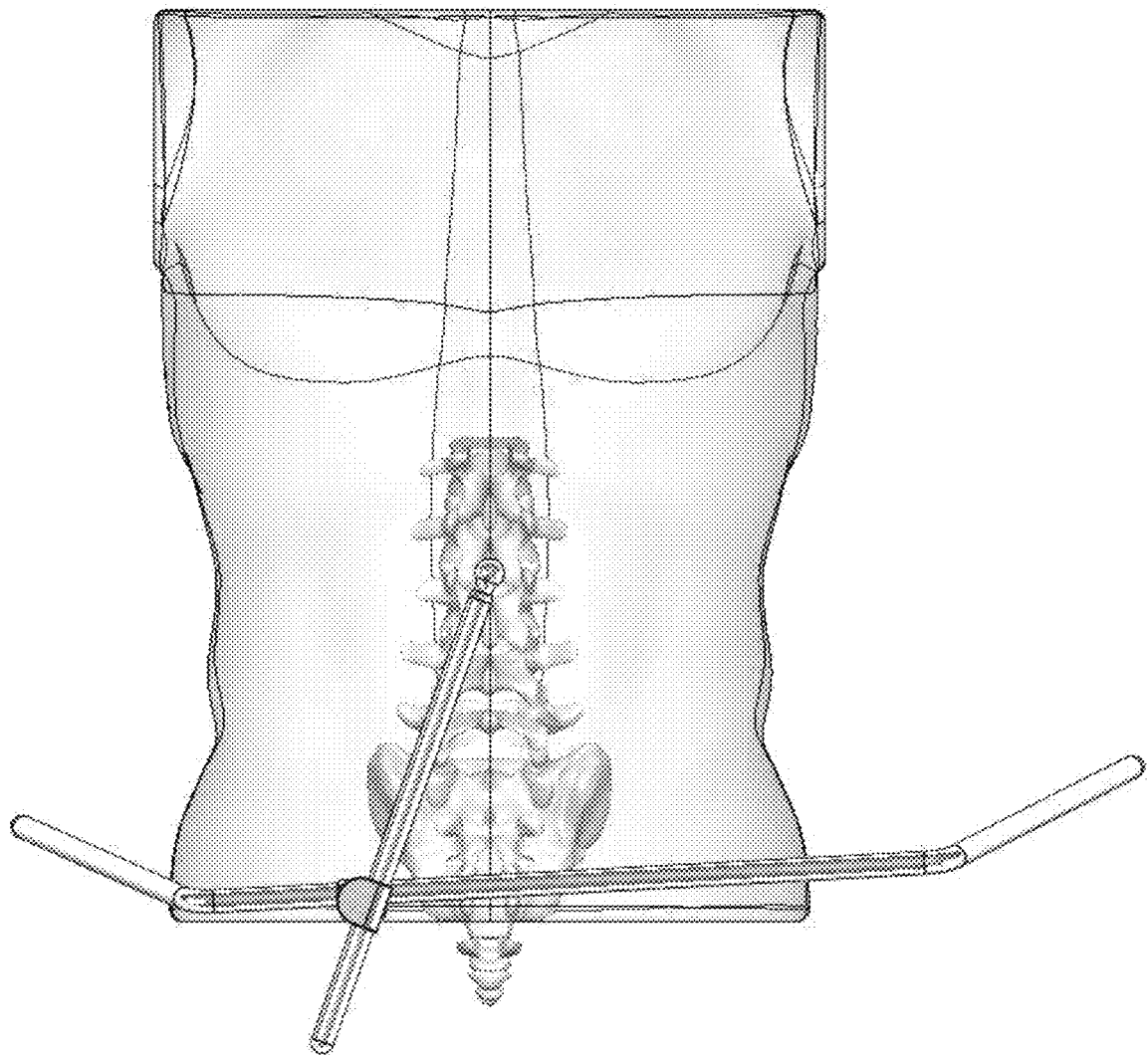
FIG. 3 is a schematic showing an alternate view of a portion of a lumbar spine in the context of a frame system according to the disclosure.
Figure 4:
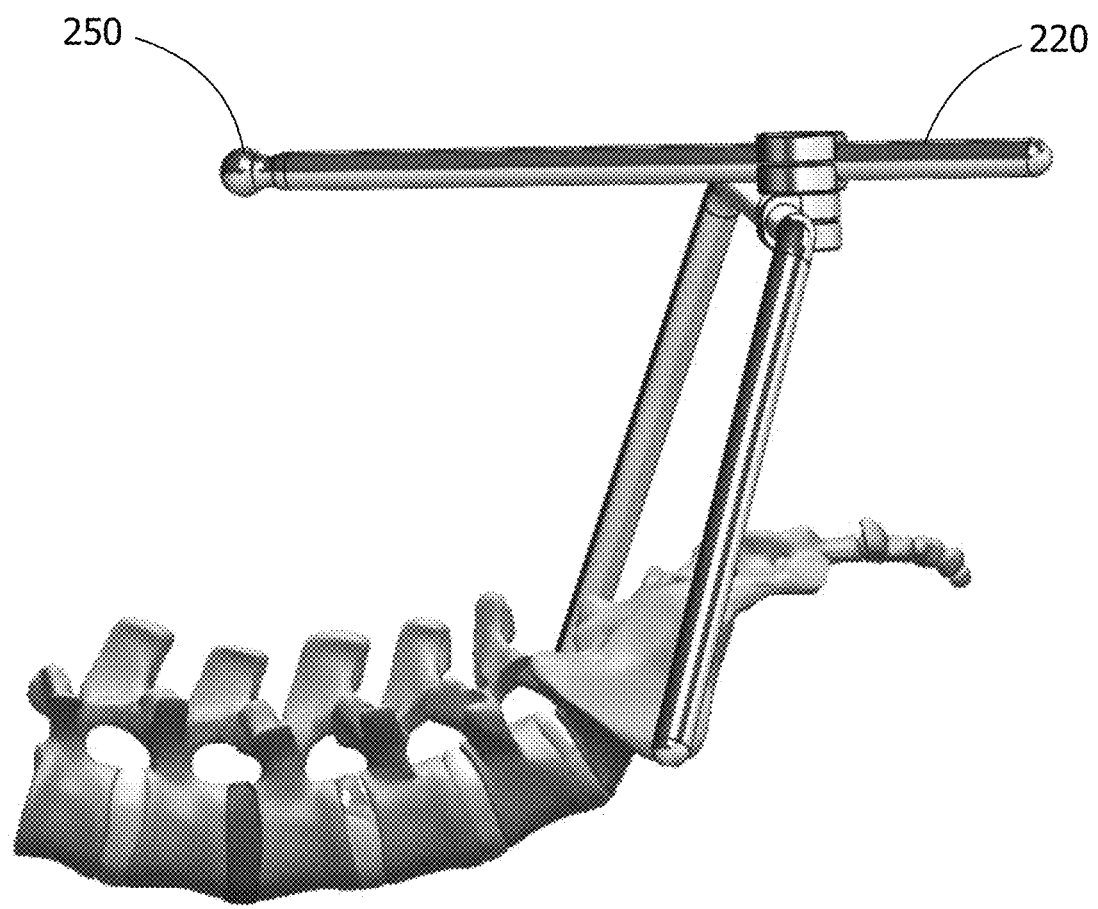
FIG. 4 is a schematic showing an alternate view of a portion of a lumbar spine in the context of a frame system according to the disclosure.

It will be appreciated that the frame components supporting the support bar need not be rigidly aligned relative to the surgical table, and indeed, as shown for example in FIG. 3, the frame components are not square with the table but due to the degrees of rotational freedom of the attachment of the support bar to the crossbar and the freedoms allowed by the spherical head, it is possible to establish and maintain the accurate positioning of the pivot point in space for following the selected trajectory to access the target tissue. Indeed, it will be appreciated that the minimal constraint on freedom is, in some embodiments, limited only by potential interference with the elongate body of the support bar at its attachment to the spherical head. One of ordinary skill in the art will appreciate that alternate shapes that are more elongate ovoids may be useful for establishing greater rotational constraints, and surface features on the head may alternately be used to create stops on rotational freedom, as well as combinations of these. In accordance with the various embodiments, the spherical head may be directly engagable with a surgical tool, or the adjustable pivot assembly may comprise a socket 280 adapted for fixation to the sphere and to one or more surgical tools.

Figure 5:
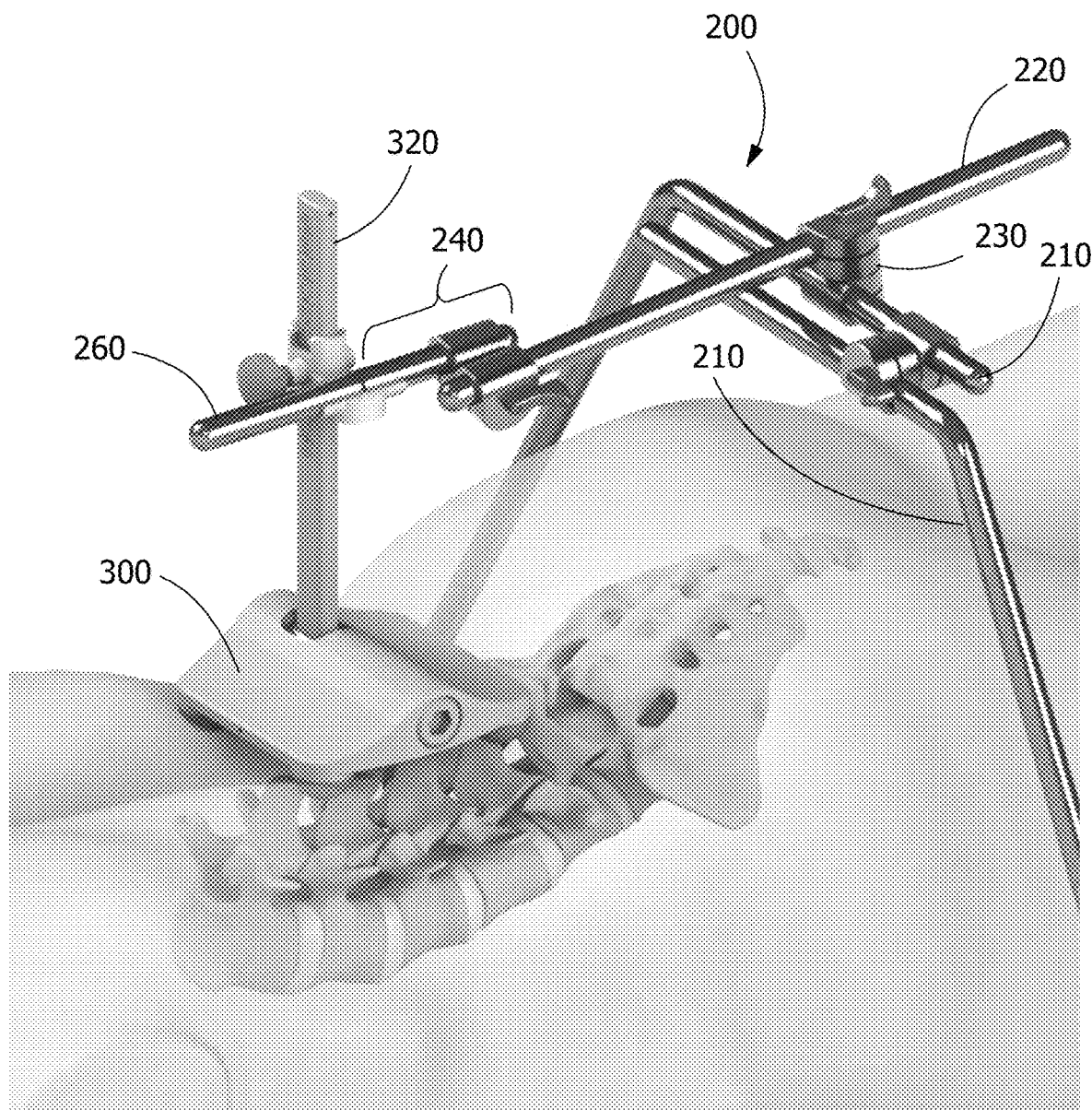
FIG. 5 is a schematic showing an alternate view of a portion of a lumbar spine in the context of a frame system and an embodiment of a guidance instrument according to the disclosure.
Figure 6:
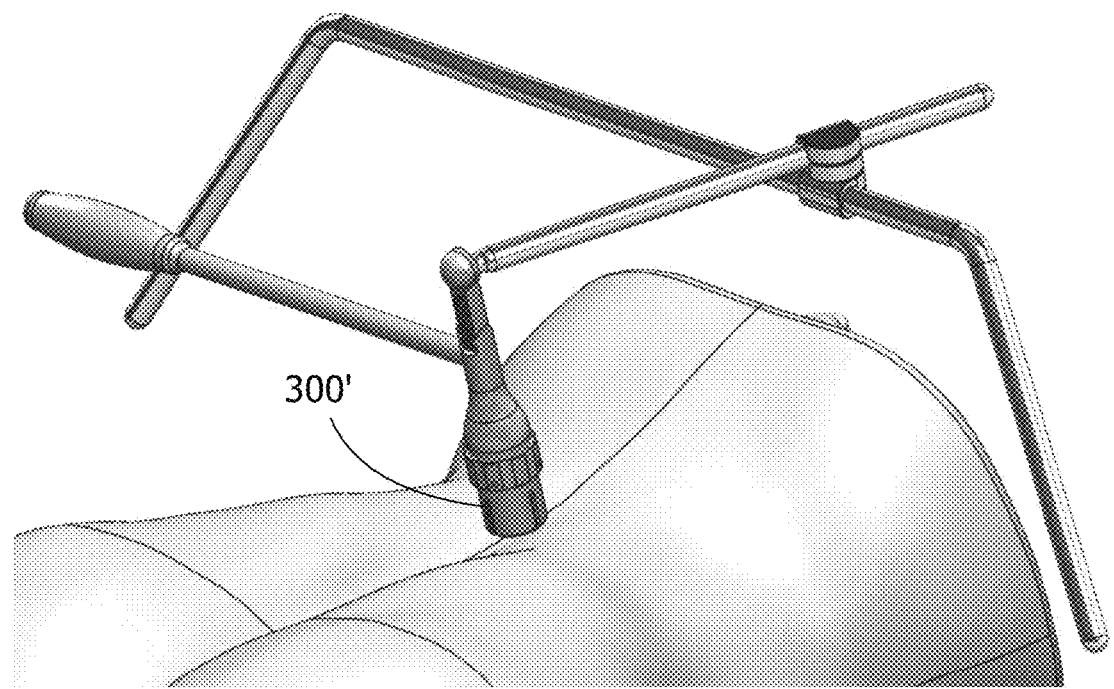
FIG. 6 is a schematic showing an alternate view of a portion of a lumbar spine in the context of a frame system and an alternate embodiment of a guidance instrument according to the disclosure.
Figure 10:
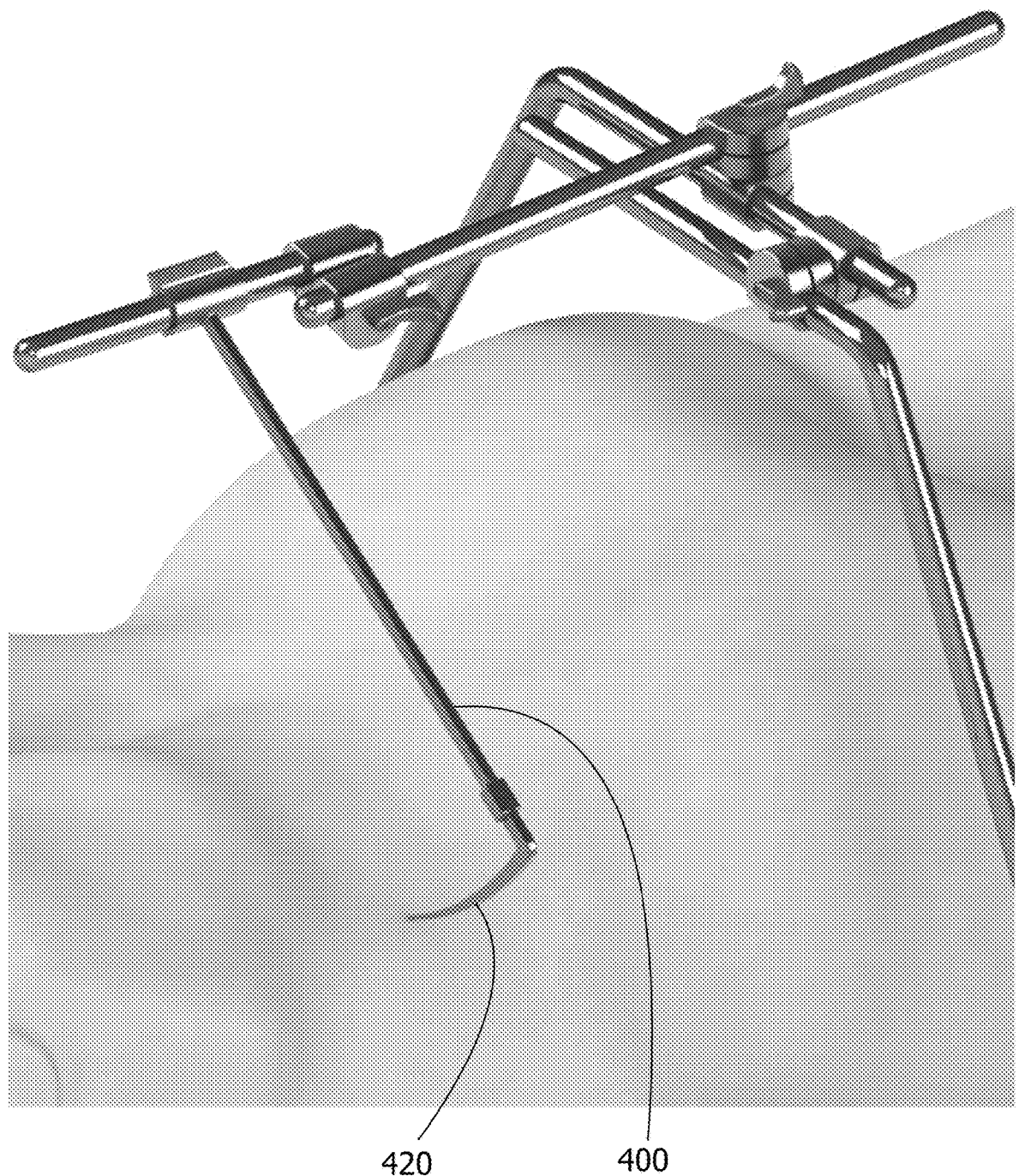
FIG. 10 is a schematic showing a view of a portion of a lumbar spine in the context of a frame system and an embodiment of a guidance instrument according to the disclosure.
Figure 11:
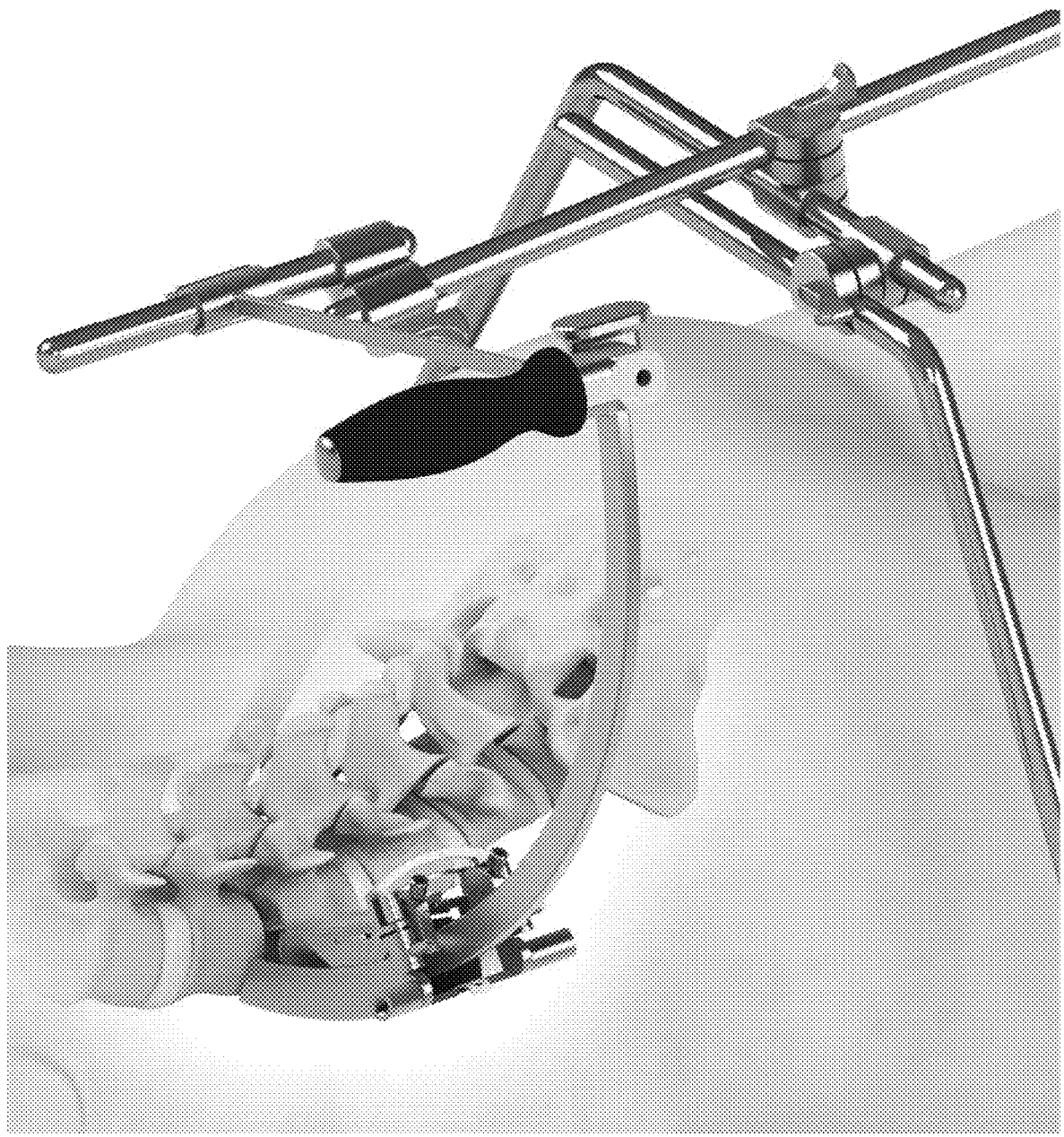
FIG. 11 is a schematic showing a view of a portion of a lumbar spine in the context of a frame system and an embodiment of a guidance instrument and a surgical tool according to the disclosure.
Figure 12:
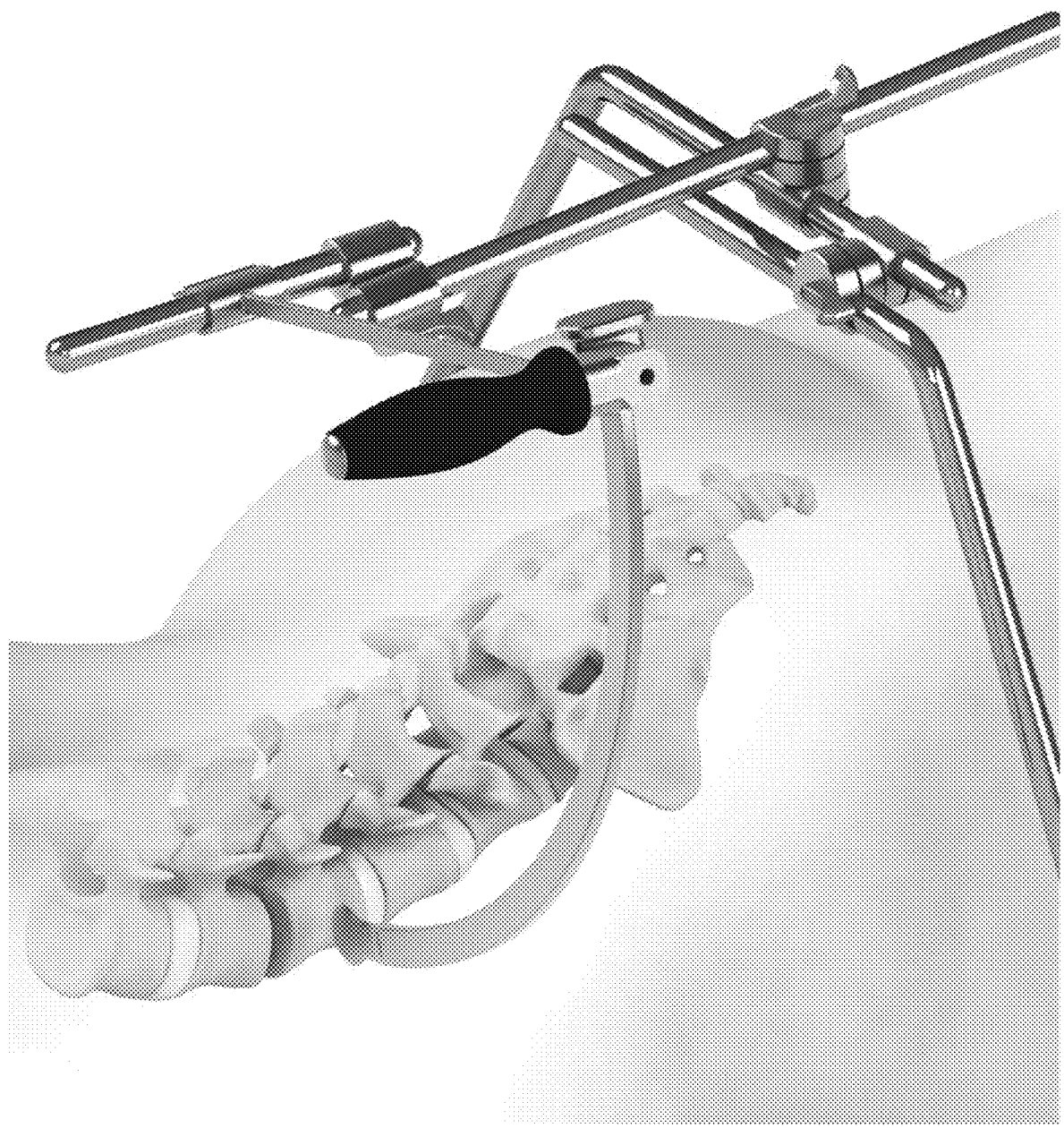
FIG. 12 is a schematic showing a view of a portion of a lumbar spine in the context of a frame system and an embodiment of a guidance instrument and a surgical tool according to the disclosure.
Figure 13:
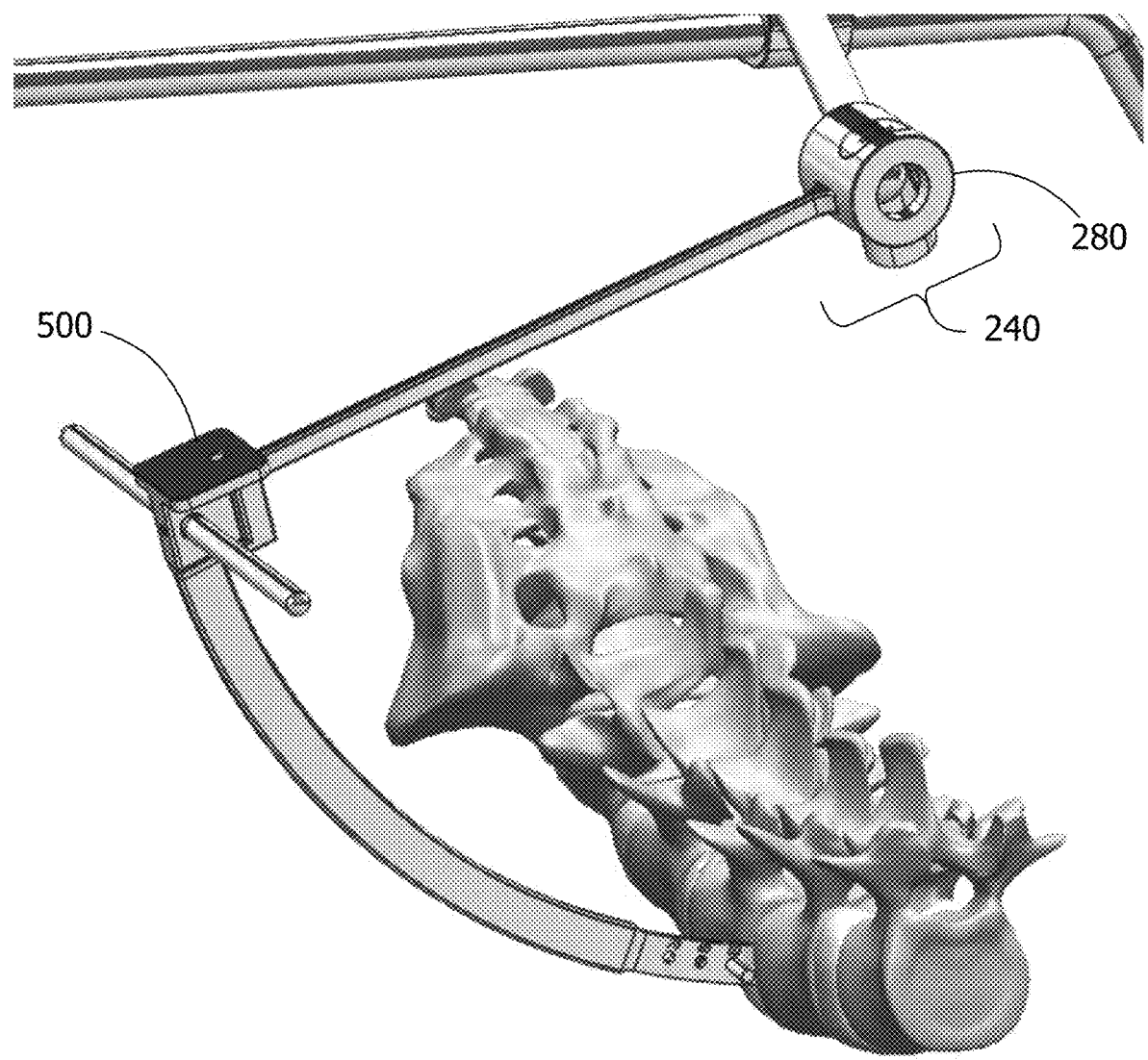
FIG. 13 is a schematic showing a view of a portion of a lumbar spine in the context of a frame system and an embodiment of a guidance instrument and a surgical tool according to the disclosure.

Referring now to FIG. 5, in another exemplary embodiment, the support bar is configured with an adjustable pivot assembly 240 comprising a sleeve that enables slidable adjustment along the axis of the support bar and rotational adjustment around the axis of the support bar. In some such embodiments, the assembly may include an extension rod 260. In accordance with some embodiments, as shown in FIG. 10, the frame is further affixed with an arcuate instrument that is pivotally mounted on the support bar and rotates around the axis of the cross bar such that its trajectory can be aligned to transect the center of the disc space (AP centerline) when the crossbar is positioned at a selected vertical height. In use, fixation to the frame enables maintenance of the selected vertical height and trajectory of the instrument's path, and application of banging or concussive force on the arcuate pointer will direct an instrument attached to the pointer into contact with the patient's tissue while the frame system largely dissipates the force so as to minimize concussive force delivery directly to the patient.

A surgical instrument assembly includes a guidance frame system comprising. The frame system includes at least one rigid cross bar, at least one adjustable connector slidably engaged on the rigid cross bar, at least one a rigid support bar interconnected with and adjustably positionable relative to the rigid cross bar, and an adjustable pivot assembly attachable or fixed to the support bar. The rigid cross bar is adapted for fixed attachment to a surgical support surface, such as a table, for example a Jackson table. The rigid support bar is adapted at a first end for slidable and lockable engagement with the adjustable connector and is adapted at a second end for lockable engagement with one or more of the adjustable pivot assembly and a surgical tool. The adjustable connector is adapted for engagement with the cross bar, and is adjustable to allow positional adjustment of an engaged rigid support bar by one or more ranges of motion. For example, actuation can result in perpendicularly arranged bars where the support bar pitches downward or upward in a vertical direction at its distal end that is not attached to the support rod. In another example the support rod may be rotated from between a perpendicular to a near parallel alignment with the cross bar. Or the support bar may be translated either along the long axis of the cross bar, or transverse to its axis, or combinations of these. Or the support bar may be raised or lowered along a vertical axis relative to the cross bar such that its vertical height relative to the support surface changes.

Thus, in various possible embodiments, the movement of the support bar relative to the cross bar by actuation of the adjustable connector may include one or more of translational adjustment along an elongate axis and between a first and second end of the rigid cross bar; translational adjustment along a horizontal axis that is perpendicular to the elongate axis of the rigid cross bar; translational adjustment along a vertical axis that is perpendicular to the elongate axis of the rigid cross bar; rotational adjustment around the elongate axis of the rigid cross bar; rotational adjustment around the vertical axis that is perpendicular to the elongate axis of the rigid cross bar; and rotational adjustment around the horizontal axis that is perpendicular to the elongate axis of the rigid cross bar. The frame system also includes one or more surgical tools selected from guidance instruments, retractors and retractor components, and tissue manipulation surgical tools, which are in some embodiments engageable with one or more of the rigid support bar and the adjustable pivot assembly.

In some embodiments, any one of the bars of the frame system and the adjustable connector and adjustable pivot assembly includes a handle configured for manipulation by a user, wherein manipulation of the handle allows the user to releasably adjust the position of any one of the bars of the frame system.

In some embodiments, the rigid cross bar is adjustable at its attachment to the surgical support surface, and wherein the rigid support bar is adjustable at the adjustable slidable connector.

In some embodiments, the surgical tool is configured for attachment at a first proximal end to one of the rigid support bar and the adjustable pivot assembly, and at its distal end with a tissue manipulation implement, wherein a distance between the proximal and distal ends defines a length of the surgical tool.

In some embodiments, the adjustable pivot assembly comprises a lockable sleeve enablable with the support rod and adapted to receive an extender rod adapted with a pivot arm that is fixed on the extender rod and is rotatable around a long axis of the extender rod, the pivot arm adapted for fixation to a surgical tool.

In some embodiments, the adjustable pivot assembly comprises a spherical head on the second end of the support rod and an engagable socket member that is adapted to engage with the spherical head, the socket member adapted for fixation to a surgical tool.

In some embodiments, adjustment and locking of the support bar connector effectively fixes in space the position of the adjustable pivot assembly, and thereby fixes the point of attachment of the surgical tool, and wherein the position of the pivot assembly is selected to direct a tissue manipulation implement portion of the surgical tool into contact with a target site in or on a surgical subject on the surgical support surface.

In some embodiments, adjustment and locking of the support bar connector effectively fixes in space the position of the adjustable pivot assembly, and thereby fixes the point of attachment of the surgical tool, and wherein the position of the pivot assembly is selected to direct a tissue manipulation implement portion of the surgical tool into contact with a target site in or on a surgical subject on the surgical support surface.

In various embodiments, the surgical tool is selected from shims, osteotomes, tissue distractors, and inserters, and instruments for manipulation of one or more of bone screws, plates, interbody devices, and artificial discs, and wherein the surgical tool comprises one or more of an actuator selected from a ratchet or gear system comprising one or more rack and pinion components, a walking beam and plates drive system, and, a threaded rod with a shift for providing rotational force to alternately drive distal and proximal movement.

The various instruments described herein below may be affixed to such frame system to achieve positioning of a spinal access system, such as the modular retractor system described herein, and manipulation of tissue in preparation for implant delivery.

Surgical Instruments

Trajectory Guide Arm

In some embodiments, a trajectory guide arm is used for one or more of establishing initial entry into the skin (i.e., incision into a patient's anatomy), establishing access to a particular target tissue (e.g., targeting entry point into the lateral margin of a spinal disc space), fixing positioning of a tissue preparation or tissue manipulation tool, and securing and stabilizing delivery of implants, and combinations of these.

Referring generally to the drawings, for example in FIGS. 10-17, the depicted modular retractor, incision guidance, and tissue preparation instruments each includes a curvilinear components adapted for posterior incision entry and lateral spinal access. It will be appreciated by one of skill that the radius of the instruments, as described herein below, are influenced by the selected radius of curvature for achieving lateral access to the disc space. Generally, the greater the radius, the flatter the channel and instruments, dictating a more ventral incision site on the patient, and the smaller the radius, the steeper the channel and instruments, dictating a more dorsal incision site on the patient. Thus, the points of access in the spine relative to the anterior to the center line to the posterior edge of the disc space may vary to accommodate the selected radius of curvature or lack thereof and enable delivery of an implant along the modular retractor to align with the centerline of the disc space.

Without being limiting, the radius of curvature of instruments according to the disclosure may be within a range from about 0 cm to about 60 cm, and more particularly from about 5 cm to about 25 cm, and in some embodiments the radius may be selected from one of 15 cm, 17 cm, 17.5 cm, 18 cm, 22 cm, 22.5 cm, and 25 cm. Of course other radii are possible within the range from 0 cm to more than 60 cm, including 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and incremental fractions thereof including 0.1, 0.2, 0.3, 0.4, 0.5, 0.6, 0.7, 0.8, 0.9 cm.

Incision Guidance Instrument

Figure 7:
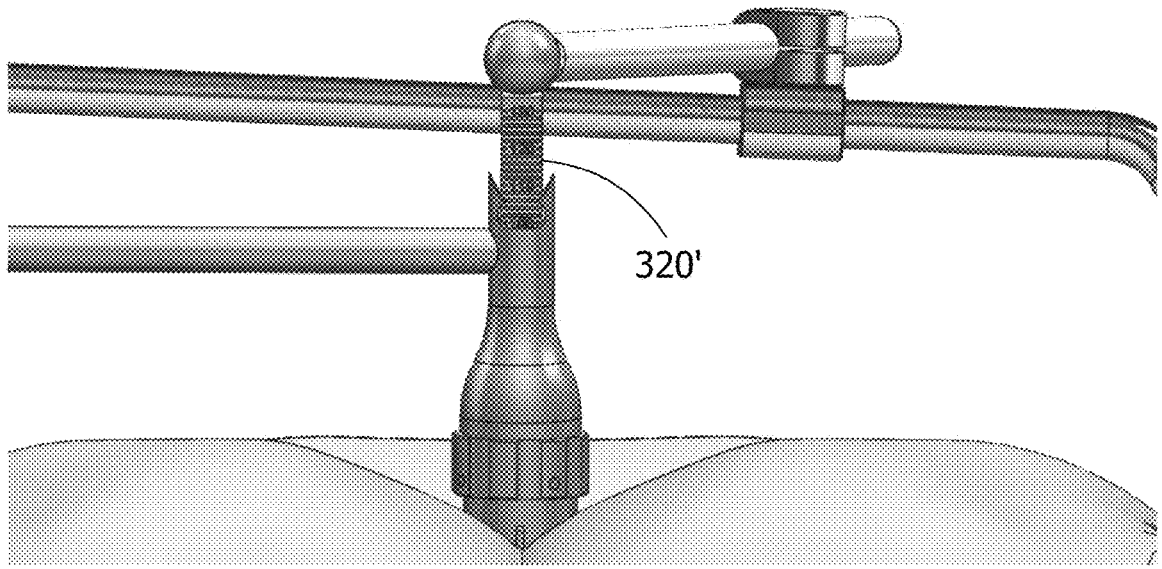
FIG. 7 is a schematic showing an alternate view of a portion of a lumbar spine in the context of a frame system and an embodiment of a guidance instrument according to the disclosure as shown in FIG. 6.

In some embodiments of the surgical techniques, an incision guidance instrument is used for selecting a desirable incision site for insertion of the modular retractor system to achieve placement at the desired location relative to a target spinal intervertebral space. Referring again to the drawings, FIG. 5 and FIG. 7 show elements of two alternate embodiments of an incision guidance instrument 300 and 300' in accordance with the disclosure, the instrument positioned relative to a portion of a lumbar spine in the context of human anatomy. The instrument is useful, in particular, for aiding in the selection of incision site on a patient, particularly on a patient in a prone position for whom a lateral mode of access to a spinal vertebra or vertebral space is desired.

Referring now to FIG. 10, the guidance instrument allows precise spatial positioning of the point of articulation, in some embodiments, rotational translation, of a substantially linear pivot arm that extends on an axis that is parallel to the lateral dimension of the position indicators and is adjustable and lockable vertically. In the depicted embodiment, the pivot arm is attached at a first end to the vertical extender and pivots from a position that is parallel with the extender to a position that is perpendicular to the extender and parallel to the plane of the base. In various embodiments, such as in the alternate embodiment shown in FIG. 10, a pivot arm 400 has an arcuate pointer 420 extending from a free end of the pivot arm. The arcuate pointer is formed of radio opaque material, allowing its detection by radiography, such as for example, X-Ray fluoroscopy. The arcuate pointer is attached to the pivot arm, and may be adjustably attached to enable adjustable extension therefrom. The guidance instrument may also comprise a support bracket adapter for attachment to a support bracket fixture that is remote from the surgical field.

It will be appreciated that the guidance instrument may be used for other surgical contexts beyond the spine, taking advantage of the device's features to identify a desired position within a patient relying on the geometric relationship of the indicators and the arcuate pointer to select an incision site. In use, the guidance instrument is positioned on the surgical subject and under fluoroscopy to confirm collinear alignment of one or more indicators with target tissue.

For example, AP fluoroscopy is used to confirm collinear alignment of one or more indicators with the spine along the sagittal plane, and lateral alignment with the target disc space along the transverse plane.

Figure 8:
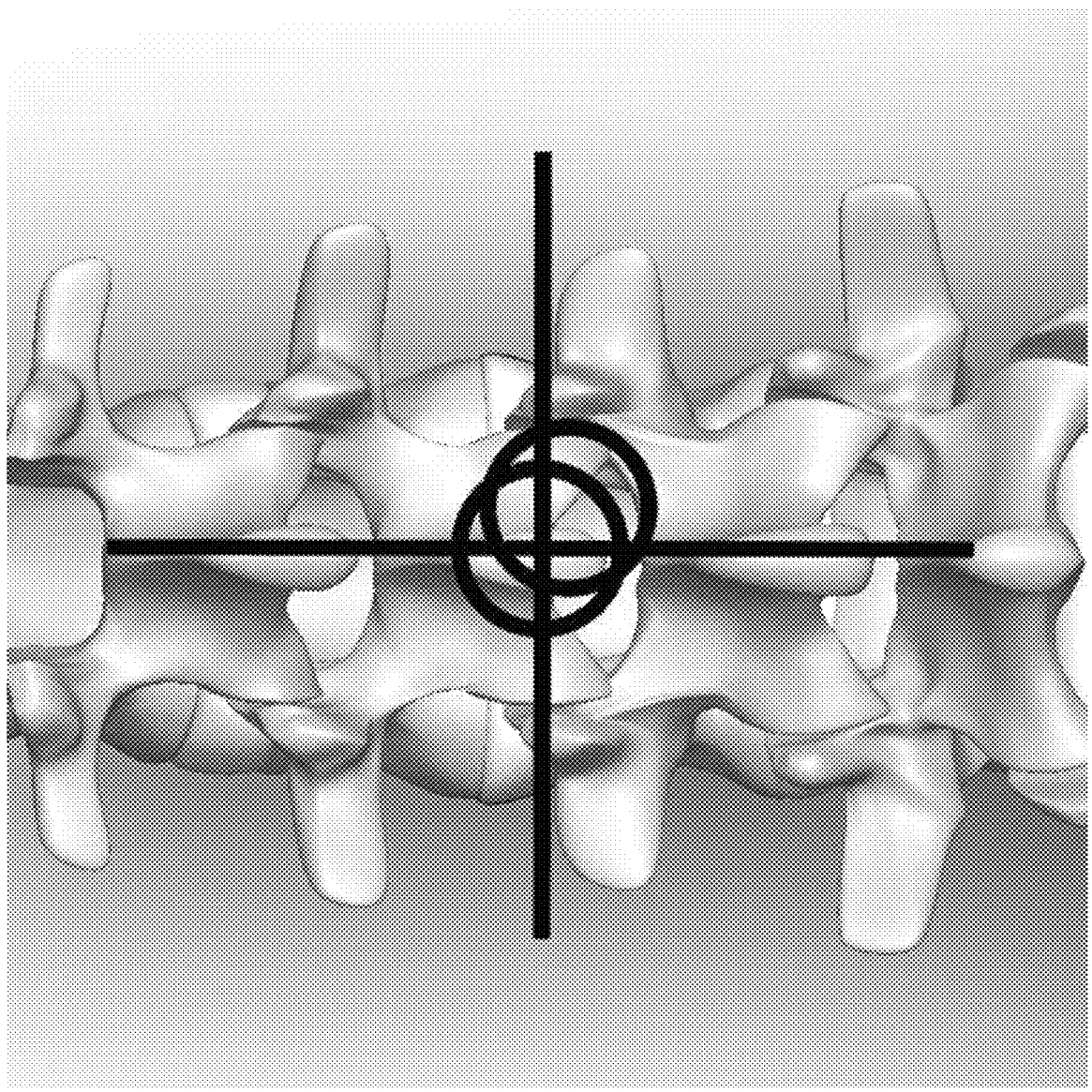
FIG. 8 is a schematic depicting non aligned indicators for surgical positioning relative to a portion of a lumbar spine.
Figure 9:
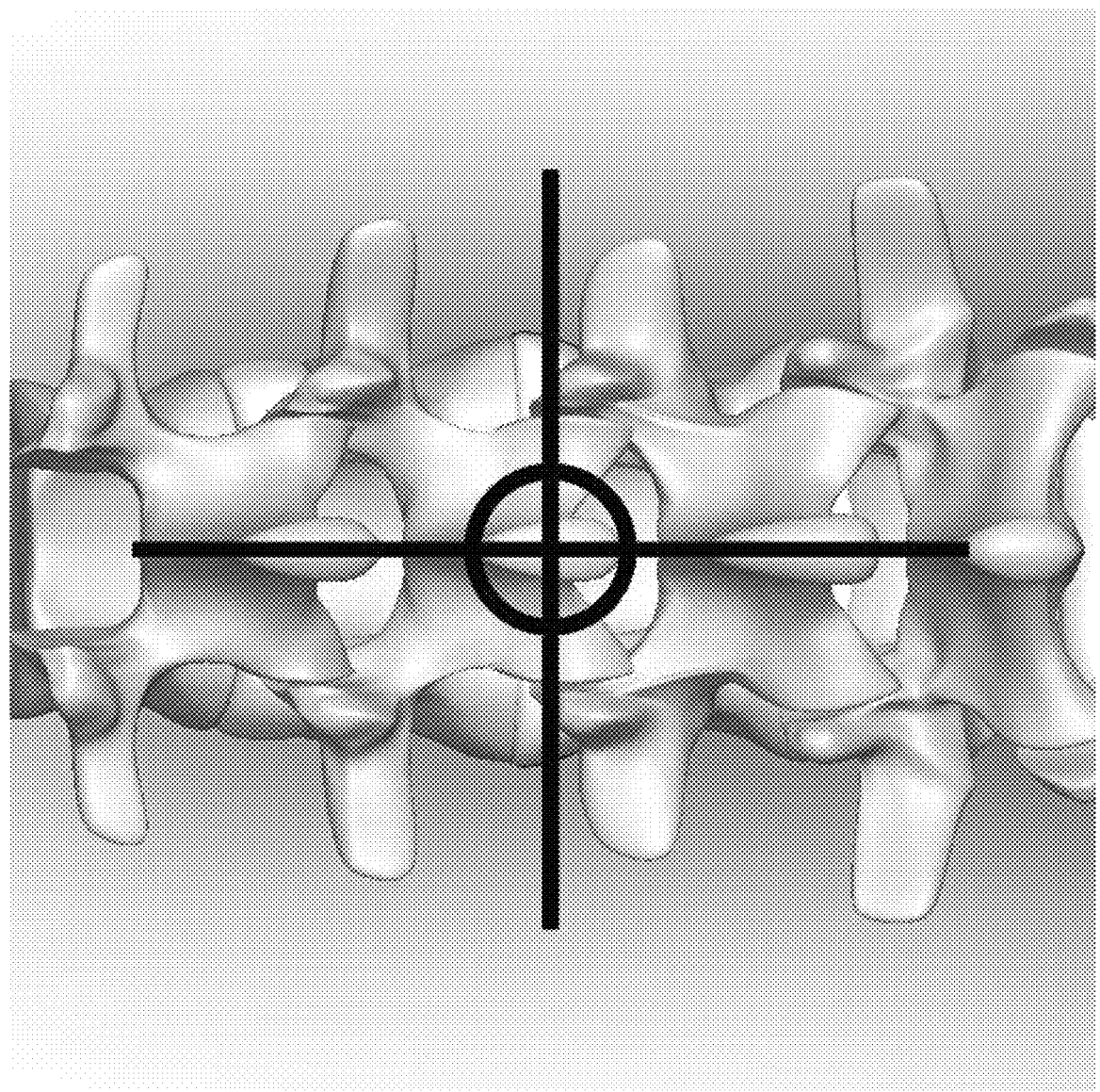
FIG. 9 is a schematic depicting aligned indicators for surgical positioning relative to a portion of a lumbar spine.

Referring again to FIG. 7, the guidance instrument includes a support base formed of essentially radio translucent material. The base is generally cylindrical and the instrument is adapted at its upper end for engagement with a support bar having a spherical head enabling polyaxial adjustment of position prior to locking. Referring again to FIG. 5, the alternate embodiment as depicted has a base that is generally square or rectangular and the instrument is adapted at its upper end for engagement with a support bar having a rotational sleeve as described herein above. In the various embodiments, to aid in the orientation of positioning, the base of the guidance instrument is adapted with crosshairs, and in some such embodiments, is embedded with crosshair-oriented position indicators that are radiopaque, the body of the instrument being radiolucent. FIG. 8 and FIG. 9 show schematic representations of crosshairs that can be visualized radiographically, FIG. 9 showing a single set of crosshairs, and FIG. 8 depicting crosshairs of vertically aligned crosshairs that are at different vertical positions on the instrument, enabling precision alignment of the crosshairs to the spine on the plane of the base and at the upper end of the instrument along its vertical dimension.

According to the various embodiments, when the base of the guidance instrument is placed in the intended orientation relative to the target tissue, such as the spine, the position indicators extend in superior to inferior and transecting lateral dimensions and are formed of radio opaque material. The instrument also includes a vertically adjustable depth indicator that extends from an upper surface of the support base and is desirably formed of essentially radio-translucent material. In various embodiments, the depth indicator includes a vertically translatable extender with graduated markings in conventional units of measure, or alternatively markings indicating a predetermined position relative to a position of the patient's anatomy. The extender may include an extender lock.

In various embodiments, the height of the vertically adjustable extender 320 320' is selected to enable travel of the incision guidance instrument pivot arm along the desired radius of curvature whereby the arcuate pointer would enter the disc space adjacent to a vertebra of interest at a position that is dorsal to the midline of the disc along the frontal plane, at approximately 30% of the overall disc height (in the AP dimension) from the posterior disc margin, wherein the disc height is measured radiographically, for example using CT radiography, as the distance between the anatomical posterior and anterior disc margins.

It will be appreciated that the locus of entry into the disc space in the AP dimension is selected based upon the particular anatomical features of a human spine and the dimensions of the modular retractor components. Thus, it will be further appreciated that in other embodiments, the entry point for achieving centering relative to another target tissue, including the spine and other anatomical structures within a body, may be varied so as to achieve desired positioning. Thus, as applicable to the spine, the above disclosed selected point of entry at a position that is dorsal to the midline of the disc along the frontal plane, at approximately 30% of the overall disc height (in the AP dimension) from the posterior disc margin is non limiting. Indeed, as otherwise described herein, targeting may be selected for entry into the disc at a position other than 30% of the disc height.

Thus, in other embodiments wherein access to the spine is desired, the entry position may be more dorsal or more ventral, and may be anywhere within the range from 1% to 99% of the overall disc height from the posterior disc margin, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99%.

More particularly, the height of the attachment point of the pivot arm to the vertically adjustable extender is determined based on one or more anatomical measurements obtained radiographically or manually relative to a vertebra of interest, including one more of a spinous process, anterior and posterior vertebral margins, and associated disc margins. According to some such embodiments, the measurements are selected from distance from a skin surface above the spinous process to the spinous process, distance from the top of the spinous process to the anterior margin of the disc, and distance from the top of the spinous process to the posterior margin of the disc.

In one representative example, wherein the incision site is being selected so as to establish a trajectory to the center of the disc, the distance between the center of the disc (determined, for example, using a CT radiograph—typically about ½ the distance between the anterior and posterior disc margins) to the top of the spinous process is measured, and the distance between the top of the spinous process to the top of the skin is measured, and these figures are added together to establish the total height of the guidance pivot arm rotational center from the center of the spine.

Once the height of the pivot arm is set, lateral fluoroscopy is used to confirm the contact point of the arcuate pointer at the center of the disc space in the SI dimension, and is point of contact on an external surface of the subject's skin is selected as the incision site. In various embodiments of the guidance instrument the arcuate pointer has a radius of curvature from about 5 to 50 cm, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50, and incremental fractions thereof including 0.1, 0.2, 0.3, 0.4, 0.5, 0.6, 0.7, 0.8, 0.9 cm.

Instruments for Tissue Preparation

This disclosure provides a suite of tissue manipulation instruments that enable access to and manipulation of tissue with minimal invasion of tissue, and in certain embodiments, when used with the rail and bolster system as previously described herein, these instruments reduce or eliminate the percussive techniques that are common in most spinal surgeries. Of course, it will be understood that the instruments may be adapted for use in surgeries other than on the spine of an animal, and while representative embodiments are shown as curvilinear, other rectilinear embodiments are encompassed within the scope of the invention and may be useful for spinal and other applications.

Figure 14:
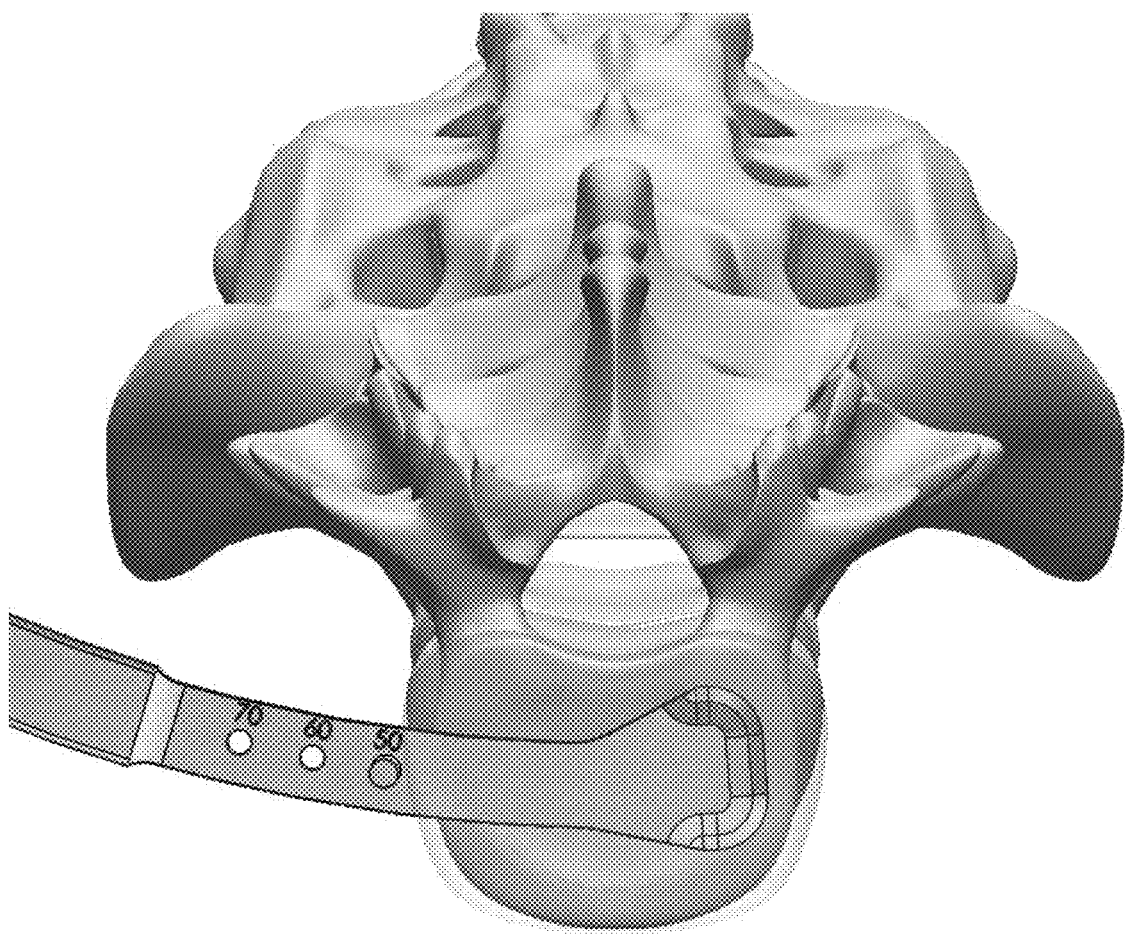
FIG. 14 is a schematic showing a tissue manipulator blade component of a surgical tool in accordance with the disclosure positioned relative to a portion of human anatomy.
Figure 15:
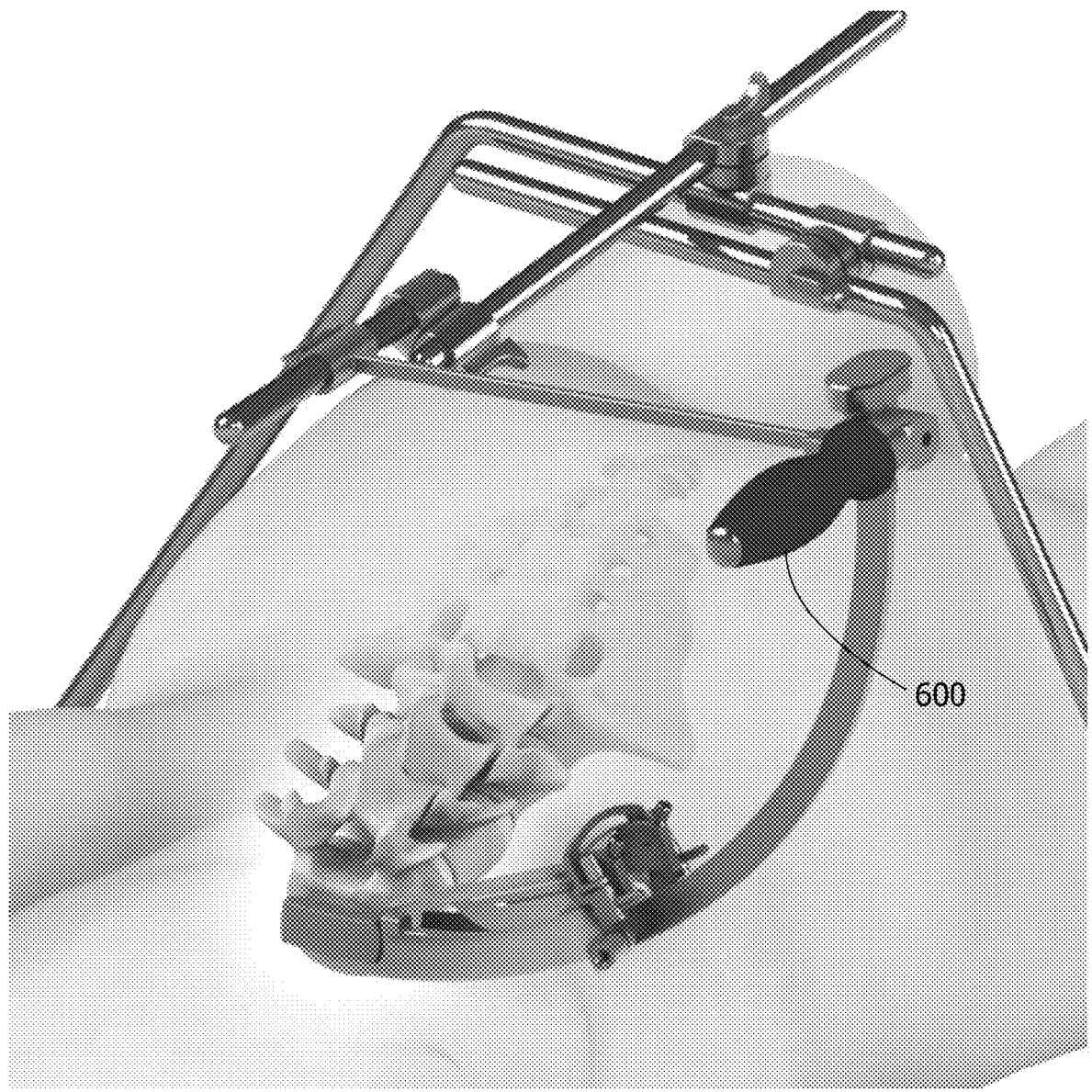
FIG. 15 is a schematic showing a view of a portion of a lumbar spine in the context of a frame system and an embodiment of a guidance instrument and a surgical tool according to the disclosure.
Figure 16:
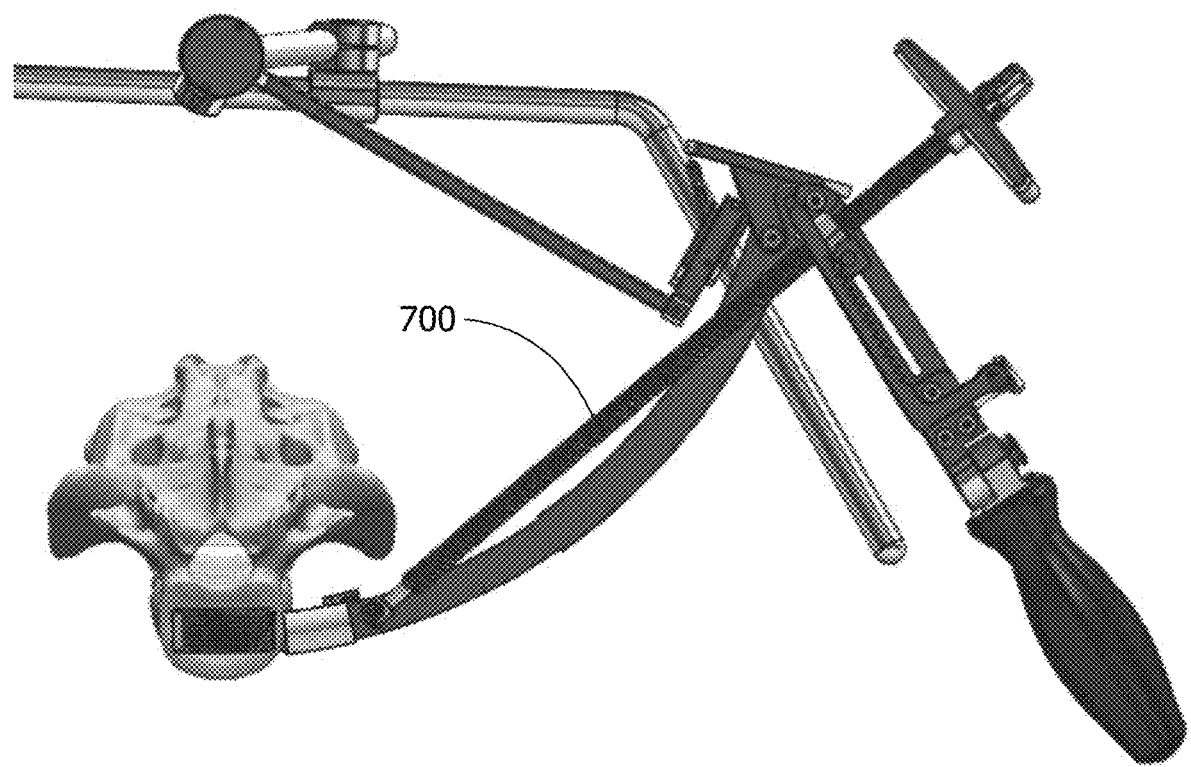
FIG. 16 is a schematic showing a view of a portion of a lumbar spine in the context of a frame system and an embodiment of a guidance instrument and a surgical tool according to the disclosure.
Figure 17:
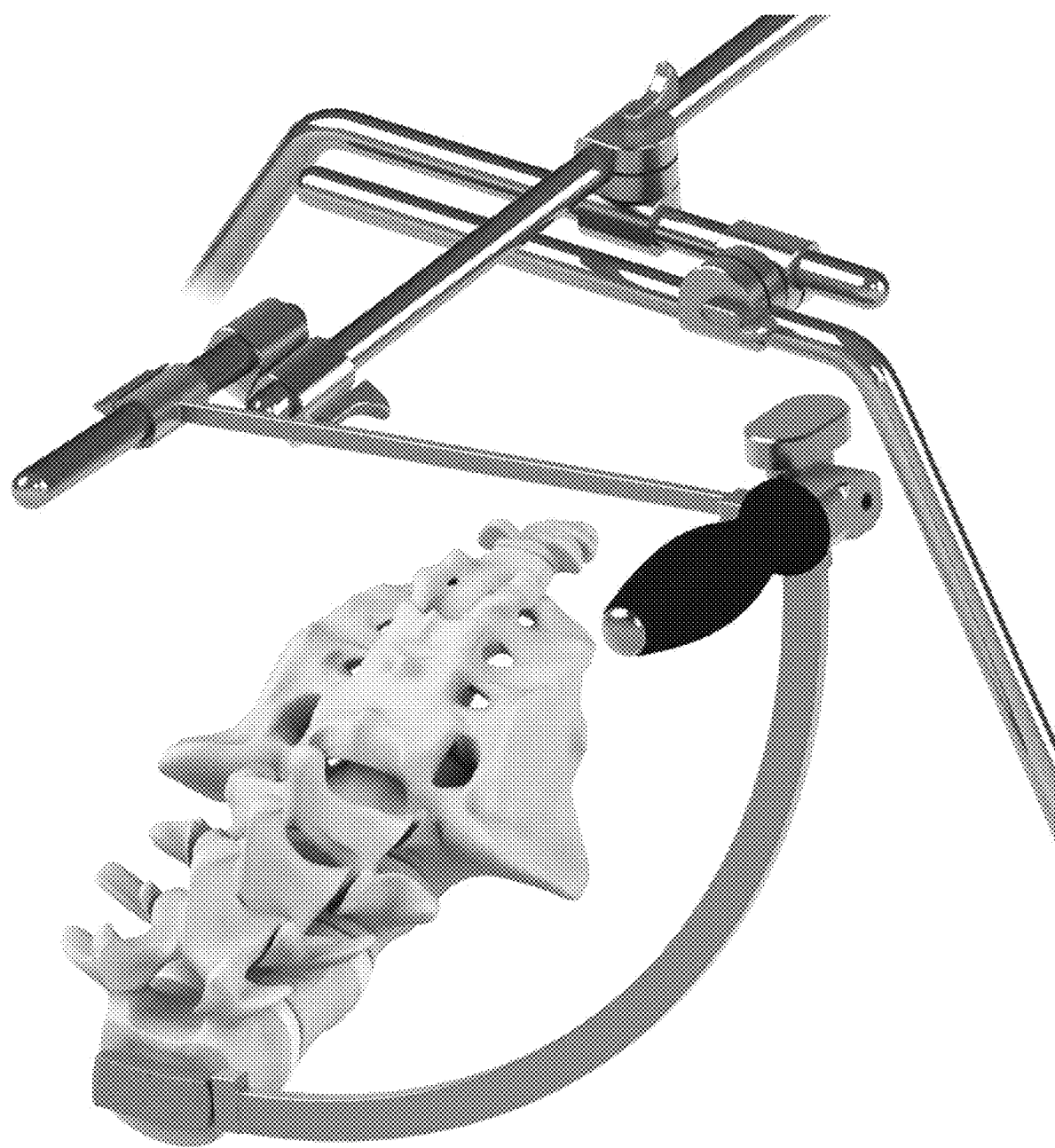
FIG. 17 is a schematic showing a view of a portion of a lumbar spine in the context of a frame system and an embodiment of a guidance instrument and a surgical tool according to the disclosure.
Figure 18:
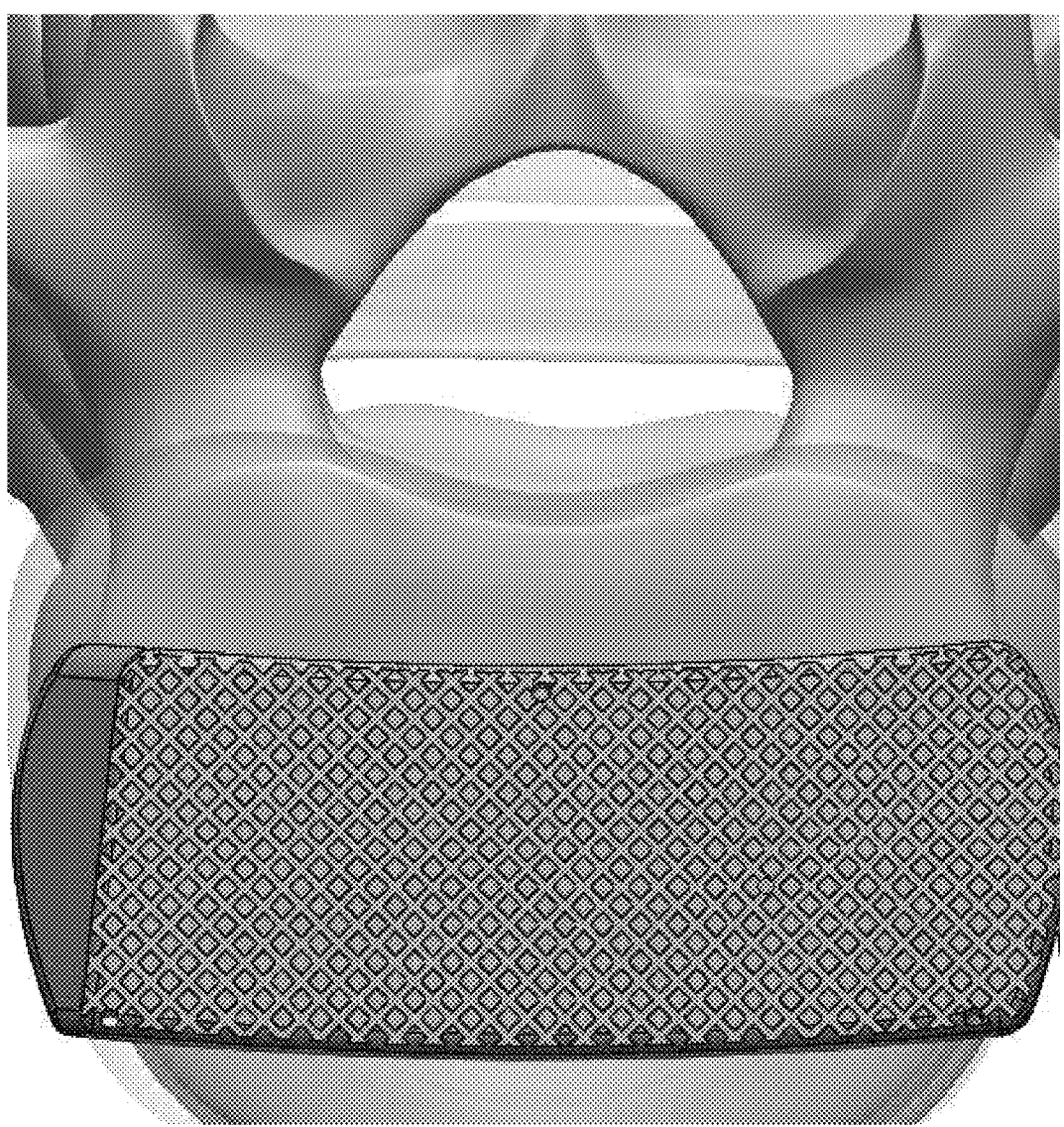
FIG. 18 is a schematic showing an interbody device inserted into a disc space in accordance with the disclosure in relation to a spine as seen along the inferior to superior axis; and, FIG. 19 shows alternate views of the interbody device shown in FIG. 18.

Referring again to the drawings, alternate embodiments of instruments are shown including in FIGS. 14-16, representative instruments comprising cutting blades for penetrating tissue, such as an osteotome for cutting the disc annulus, and tamps for tamping implants into the disc space. Tissue preparation instruments according to the disclosure include proximal ends that include drive components as shown in FIGS. 17 and 18 and distal ends that include tissue engagement components that include one or more tissue manipulators. The proximal end extends out of the surgical field and the distal end is insertable in the surgical field. In various embodiments, a tissue preparation instrument has a drive mechanism to drive distal and proximal movement of the insertion assembly for manipulating target tissue. In some embodiments, the drive mechanism includes a strike plate 500, handle 600 or other surface. In some embodiments, the drive mechanism is selected from a ratchet or gear system comprising one or more rack and pinion components, a walking beam and plates drive system, and, a threaded rod 700 with a shift for providing rotational force. In some threaded rod embodiments, the drive component includes a threaded element affixed to the housing that is adapted to receive and engage with the threaded rod. In some such embodiments, the threaded element is a threaded bore. Rotation of the insertion rod within the threaded element results in movement of the insertion rod in one or the other of the distal or proximal directions. Engagement of a second tissue manipulator, such as for example, and implant directly or indirectly to the universal joint ensures that the tissue manipulator does not rotate when the insertion rod is rotated. Other known free-rotational or swivel mechanisms may be employed as alternatives to the universal joint.

Figure 19:
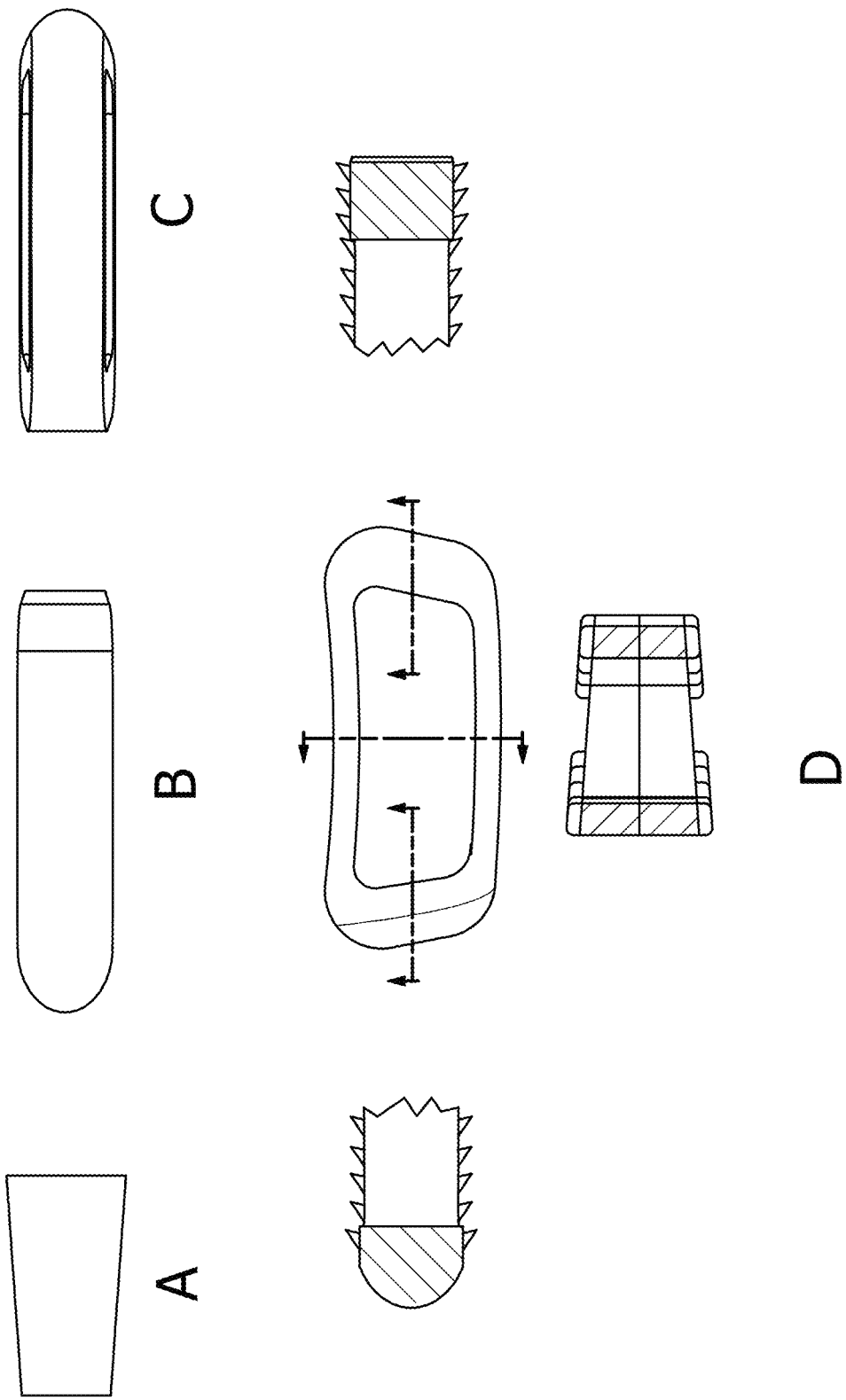

Referring now to FIG. 19, an exemplary embodiment of an interbody implant 900 insertable into the disc space using the systems and devices herein is shown. Panel D shows a side view of the implant, having an upper edge, lower edge on the bottom, leading edge on the left, trailing edge on the right, and with a center void space for optionally use of graft material, on the left side a tapered leading edge, the implant having an overall curved shape, with a generally concave curve on an upper edge for orientation toward the posterior of the spine, and convex curve on a lower edge for ordination toward the anterior of the spine, and optional teeth, knurling or other textural features on at least a portion of the face of the implant. In some embodiments the implant is lordotic, while in others it is not. Referring to panel A, a view from the trailing edge, the lordotic shape which is generally wedge can be seen in the depicted embodiment. Referring to panel B, in a view from the top edge, the tapered leading edge can be seen and the flare of the lordotic shape from the top toward the bottom can be seen. Referring to panel C, in a view from the bottom edge, the wider bottom can be seen as an aspect of the lordotic shape, with the tapered leading edge oriented toward the right.

Example 1: Representative Surgical Technique Using the Frame and Surgical Instruments A representative embodiment of a surgical technique includes the following steps, the order of which is not intended to be limiting:

Position the Patient and Establish Incision Site

Position patient prone (and generally parallel to the floor) on suitable surgical table. Obtain CT scan to measure ventral to dorsal height of target vertebral space.

Radiographically or directly measure with a needle or wire the posterior soft tissue depth to spinous process over target disc space. (If procedure is open, this step is not required.)

Calculate total ventral to dorsal height, and adjust incision guidance instrument guide height to enable direction of incision guidance instrument pointer to a position that is approximately 30% of the overall disc height from the posterior disc margin, based on the calculated disc height. (This is the target entry point into the disc space, dorsal to the midline of the disc along the frontal plane.) Rest exemplary represented instrument for measurement ("incision guidance instrument") on patient (either on soft tissue for a closed procedure, or on spinous process if procedure is open) and use position indicators to roughly align with the spinal axis. Visualize with AP fluoroscopy to confirm collinear alignment with the spine along the sagittal plane and lateral alignment with the target disc space along the transverse plane. Engage incision guidance instrument pivot arm to approximate centerline of the disc space and visualize with lateral fluoroscopy to confirm. As needed, adjust fluoroscope position to achieve complete alignment of the image path and the incision guidance instrument, as confirmed in the fluoroscopy image. Mark skin to indicate cranial to caudal spinal midline, position of incision guidance instrument on the patient, and incision site to enable access at the target disc entry point.

Incision and Soft Tissue Dissection

Incise skin in a dorsal to ventral orientation, an exemplary incision width being approximately 4 cm. Using a Bovie, dissect through the subcutaneous tissue and muscles, and puncture through the Transversalis fascia into the retro peritoneum with a Kelly clamp. Manually enlarge the fascia incision and dissect the retro peritoneum towards psoas muscle, palpating the transverse process to confirm the posterior margin of disc space. Optionally, insert and engage retraction instrument(s), such as a bilateral speculum, in a cranial to caudal orientation to further expand the surgical field and expose the spine and associated soft tissue. Manually confirm nerve position relative to the psoas muscle to establish dissection point, and provisionally dissect.

Retractor Placement and Use of Surgical Tools

In some embodiments using a modular retractor as shown in some representative drawings, such as a curvilinear retractor, positioning and placement involves placing a first retractor having a distal end substantially adjacent to an anterior aspect of a spine at a target intervertebral space identified using the targeting method described above between a first vertebra and an adjacent vertebra, sliding adjacent to the first retractor a second retractor, the second retractor having a distal end that is adapted for manipulating soft tissue, manually directing the second retractor towards the spine and displacing the second retractor posteriorly and away from the first retractor so as to lift the soft tissue posteriorly/dorsally to enhance visualization of the spine, assembling the first and second retractors into engagement by coupling complimentary coupling elements at proximal ends of the retractors to form a channel between the two retractors having a longitudinal axis that runs distal to proximal, adjusting the coupled retractors pivotally around a pivot axis at their proximal ends to displace the distal ends of the retractors away from one another into an open position, and locking.

According to such embodiments, the method may also comprise selecting a tissue preparation device, affixing it the surgical frame on the adjustable pivot assembly, and proceeding with one or more of the following steps in the provided or any other order, including, inserting the tissue preparation device into the channel guided by the articulation path established by the adjustable pivot assembly and into contact with the target vertebral space, the tissue preparation device fitted with a cutting instrument for penetrating a annulus of a disc within the target vertebral space, and actuating the drive component such as an impact plate on the tool to direct the cutting instrument into contact with the target vertebral space to penetrate the annulus; actuating the drive component to withdraw and replace the cutting instrument with another cutting instrument for penetrating a contralateral annulus of the disc within the target vertebral space, actuating the drive component to insert the tissue manipulator into contact with the target vertebral space to penetrate the contralateral annulus.

According to such embodiments, the method may also comprise actuating the drive component to withdraw and replace the cutting instrument with a distraction paddle that is adapted for rotating within the disc space to enhance distraction of the adjacent vertebrae, actuating the drive component to insert the tissue manipulator into contact with the target vertebral space to deliver the paddle distractor which is actuated to enhance distraction of the adjacent vertebrae; actuating the drive component to withdraw and replace the distraction paddle with an endplate scraper, and actuating the drive component to insert the tissue manipulator into contact with the target vertebral space to deliver the scraper which is actuated to withdraw disc material from the disc space. According to such embodiments, the method may also comprise actuating the drive component to withdraw and replace the endplate scraper with an implant trial, and actuating the drive component to insert the tissue manipulator into contact with the target vertebral space to deliver the implant trial to determine implant size. According to such embodiments, the method may also comprise actuating the drive component to withdraw and replace the implant trial with an implant, actuating the implant length adjuster to optimize centering of the implant in the disc space, actuating the drive component to insert the tissue manipulator into contact with the target vertebral space to deliver the implant, and actuating the release to deposit the implant in the vertebral space, and withdrawing the tissue preparation device from the channel While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A surgical instrument assembly comprising
a guidance frame system comprising,
   a rigid cross bar,
   an adjustable connector slidably engaged on the rigid cross bar,
   a rigid support bar interconnected at a first end with the rigid cross bar and adjustably positionable relative to the rigid cross bar, and
   an adjustable pivot assembly comprising a spherical head affixed at a second end of the rigid support bar, and a socket member engagable with the spherical head and adapted for fixation to a surgical tool,
wherein the rigid cross bar is adapted for fixed attachment to a surgical support surface,
wherein the rigid support bar is adapted at a first end for slidable and lockable engagement with the adjustable connector and is adapted at a second end for lockable engagement with one or more of the adjustable pivot assembly and a surgical tool, and
wherein the adjustable connector is adapted for engagement with the rigid cross bar, and is adjustable to allow positional adjustment of an engaged rigid support bar by ranges of motion that include each of:
   translational adjustment of the engaged first end of the rigid support bar along an elongate axis of the rigid cross bar and between a first end and a second end of the rigid cross bar;
   translational adjustment along a horizontal axis that is transverse to the elongate axis of the rigid cross bar;
   rotational adjustment around the elongate axis of the rigid cross bar;
   rotational adjustment around a vertical axis that is perpendicular to the elongate axis of the rigid cross bar; and
   rotational adjustment around the horizontal axis that is transverse to the elongate axis of the rigid cross bar;
a surgical tool engageable with one or more of the rigid support bar and the adjustable pivot assembly.

2. A surgical instrument assembly according to claim 1, wherein any one of the bars of the guidance frame system and the adjustable connector and adjustable pivot assembly includes a handle configured for manipulation by a user, wherein manipulation of the handle allows the user to releasably adjust the position of any one of the bars of the guidance frame system.

3. A surgical instrument assembly according to claim 2, wherein the rigid cross bar is adjustable at its attachment to the surgical support surface, and wherein the rigid support bar is adjustable at the adjustable slidable connector.

4. A surgical instrument assembly according to claim 3, wherein the adjustable pivot assembly comprises a lockable sleeve enablable with the rigid support bar and adapted to receive an extender rod adapted with a pivot arm that is fixed on the extender rod and is rotatable around a long axis of the extender rod, the pivot arm adapted for fixation to a surgical tool.

5. A surgical instrument assembly according to claim 1, wherein the surgical tool is configured for attachment at a first proximal end to one of the rigid support bar and the adjustable pivot assembly, and at its distal end with a tissue manipulation implement, wherein a distance between the proximal and distal ends defines a length of the surgical tool.

6. A surgical instrument assembly according to claim 1, wherein the surgical tool is selected from shims, osteotomes, tissue distractors, and inserters, and instruments for manipulation of one or more of bone screws, plates, interbody devices, and artificial discs, and wherein the surgical tool comprises one or more of an actuator selected from a ratchet or gear system comprising one or more rack and pinion components, a walking beam and plates drive system, and, a threaded rod with a shift for providing rotational force to alternately drive distal and proximal movement.

7. A surgical instrument assembly according to claim 1, comprising a guidance instrument for selecting an incision site for access to a spine of a surgical subject, the guidance instrument comprising;
 a support base formed of radio translucent material and comprising crosshair-oriented position indicators that extend, with reference to the spine of the surgical subject, in a superior to inferior dimension and a transecting lateral dimension and are formed of radio opaque material;
 a vertically adjustable depth indicator that extends from an upper surface of the support base and is formed of radio-translucent material, the depth indicator comprising
  a vertically translatable extender with graduated markings in conventional units of measure, an extender lock;
  a vertically adjustable and linear pivot arm that extends on an axis that is parallel to the lateral dimension of the position indicators and is adjustable and lockable vertically and which is attached at a first end to the vertically translatable extender and pivots from a position that is parallel with the vertically translatable extender to a position that is perpendicular to the vertically translatable extender,
 wherein, in use, the guidance instrument is positioned on the surgical subject and under fluoroscopy to confirm collinear alignment with the spine along the superior to inferior dimension in a plane that sagittal with respect to the spine of the surgical subject and lateral alignment with a target disc space along the lateral dimension in a plane that is transverse to an axis defined by the spine of the surgical subject, and a vertical height of the pivot arm is selected to approximate centerline of the disc space, whereby the contact point of the arcuate pointer on an external surface of the surgical subject's skin is selected as an incision site.

8. A surgical instrument assembly according to claim 7, wherein the height of the vertically adjustable extender is determined based on one or more anatomical measurements obtained radiographically or manually relative to a vertebra of interest, including one more of a spinous process, anterior and posterior vertebral margins, and associated disc margins, the measurements selected from
 distance from a skin surface above the spinous process to the spinous process,
 distance from the top of the spinous process to the anterior margin of the disc,
 distance from the top of the spinous process to the posterior margin of the disc,
 wherein the height of the vertically adjustable extender is selected to enable travel of the incision guidance instrument pivot arm along the desired radius of curvature.

9. A surgical instrument assembly according to claim 8, the guidance instrument comprising an arcuate pointer extending from a free end of the pivot arm and formed of radio opaque material, the arcuate pointer adjustably attached to the pivot arm to enable adjustable extension therefrom.

10. The surgical instrument assembly according to claim 9, the arcuate pointer having a radius of curvature from about 5 to 50 cm.

11. A surgical instrument assembly according to claim 1, comprising a modular surgical retractor comprising, a retractor body and a retractor hood, the retractor body and retractor hood each comprising a proximal end that is adapted to extend outside of the surgical field and a distal end that is adapted to extend into the surgical field, the retractor body and retractor hood engageable to form a through channel disposed between open proximal and distal ends that are defined by the proximal and distal ends of the retractor body and retractor hood, and bounded by the retractor body and retractor hood, the through channel having a central channel axis, the retractor body comprising a floor extending along a retractor body longitudinal axis, and the retractor hood comprising a body extending along a retractor hood longitudinal axis, the retractor hood having a soft tissue elevator at the distal end, and a releasable handle at the proximal end.

12. A surgical instrument assembly according to claim 11, each of the retractor body and retractor hood being independently operable to manipulate soft tissue and adapted to be adjustably and releasably coupled at their proximal ends with general alignment of their respective longitudinal axes, the retractor body and the retractor hood each comprising at its proximal end a coupling element for adjustably and releasably coupling the retractor body and retractor hood, one of the coupling elements comprising one or a plurality of fasteners, and the other of the coupling elements comprising one or a plurality of receivers,
 wherein when uncoupled, the retractor hood can be aligned with the retractor body and at least partially compressed against the retractor body, and wherein, when coupled, the retractor body and retractor hood are displaced from one another vertically and constrained to one or more of three degrees of freedom, being movable pivotally around a pivot axis at the proximal end that is perpendicular to the channel longitudinal axis, displaceable vertically from between a compressed orientation up to a pre selected displacement distance, or slidable horizontally along the channel longitudinal axis, or combinations of these.

13. A surgical instrument assembly according to claim 12, wherein the modular surgical retractor comprises one or more of the features selected from the group consisting of:
 the retractor body is substantially curvilinear along its longitudinal axis and has a radius of curvature from 5 to 50 cm;
 the distal end of one or both the retractor body and retractor hood is contoured and wherein the contour describes a concave arc that transects the retractor's longitudinal axis and has a radius of curvature from 0.5 cm to 10 cm, and wherein the contour is bounded by bosses;

the retractor hood is rectilinear along its longitudinal axis, and is either rectilinear or bowed around its longitudinal axis along at least a portion of its length;

the retractor body comprises two opposing sidewalls bounding the floor along at least part of the length of the floor, the floor and sidewalls extending along the longitudinal axis and defining a chute with an open top, wherein the retractor body sidewalls are selected from essentially planar and bowed; and, at least one of the retractor and the hood comprises at least one tissue fixation member, comprising: a retractor securement element and a tissue securement element, the retractor securement element securable to one or both of the retractor body and retractor hood, and the tissue securement element is securable to a target tissue in the surgical field and selected from a screw, a pin, a wire, an awl, and a tang.

14. The surgical instrument assembly according to claim 1, comprising:

a modular surgical retractor comprising, a retractor body and a retractor hood, the retractor body and retractor hood each comprising a proximal end that is adapted to extend outside of the surgical field and a distal end that is adapted to extend into the surgical field, the retractor body and retractor hood engageable to form a through channel disposed between open proximal and distal ends that are defined by the proximal and distal ends of the retractor body and retractor hood, and bounded by the retractor body and retractor hood, the through channel having a central channel axis, the retractor body comprising a floor extending along a retractor body longitudinal axis, and the retractor hood comprising a body extending along a retractor hood longitudinal axis, each of the retractor body and retractor hood being independently operable to manipulate soft tissue and adapted to be adjustably and releasably coupled at their proximal ends with general alignment of their respective longitudinal axes, the retractor body and the retractor hood each comprising at its proximal end a coupling element for adjustably and releasably coupling the retractor body and retractor hood, one of the coupling elements comprising one or a plurality of fasteners, and the other of the coupling elements comprising one or a plurality of receivers, wherein when uncoupled, the retractor hood can be aligned with the retractor body and at least partially compressed against the retractor body, and wherein, when coupled, the retractor body and retractor hood are displaced from one another vertically and constrained to one or more of three degrees of freedom, being movable pivotally around a pivot axis at the proximal end that is perpendicular to the channel longitudinal axis, displaceable vertically from between a compressed orientation up to a pre selected displacement distance, or slidable horizontally along the channel longitudinal axis, or combinations of these.

15. The surgical instrument assembly according to claim 14, wherein the modular surgical retractor comprises one or more of the features selected from the group consisting of:

the retractor body is substantially curvilinear along its longitudinal axis and has a radius of curvature from 5 to 50 cm;

the distal end of one or both the retractor body and retractor hood is contoured and wherein the contour describes a concave arc that transects the retractor's longitudinal axis and has a radius of curvature from 0.5 cm to 10 cm, and wherein the contour is bounded by bosses;

the retractor hood is rectilinear along its longitudinal axis, and is either rectilinear or bowed around its longitudinal axis along at least a portion of its length;

the retractor body comprises two opposing sidewalls bounding the floor along at least part of the length of the floor, the floor and sidewalls extending along the longitudinal axis and defining a chute with an open top, wherein the retractor body sidewalls are selected from essentially planar and bowed; and, at least one of the retractor and the hood comprises at least one tissue fixation member, comprising: a retractor securement element and a tissue securement element, the retractor securement element securable to one or both of the retractor body and retractor hood, and the tissue securement element is securable to a target tissue in the surgical field and selected from a screw, a pin, a wire, an awl, and a tang.

16. A surgical instrument assembly, comprising: a frame system, and a surgical tool engageable with the frame system, wherein the frame system is adapted for providing a surgical tool attachment and articulation locus that is maintained during the course of a surgical procedure to direct a fixed and repeatable delivery path for introduction and manipulation of one or more surgical instruments and implants into a surgical site in or on the patient's anatomy, the delivery path being curvilinear along an arc that is defined by a radius of curvature of the surgical tool, a length of an attachment arm of the surgical tool to the rigid support bar, and a predetermined range of articulation of the articulation locus wherein the frame system comprises a fixed frame portion affixed to a patient support table, and a support bar comprising an adjustable connector for attachment to the fixed frame portion at a point that is proximate to a first end of the support bar, the support bar comprising an adjustable pivot assembly at a point on the support bar that is proximate to a second end of the support bar, wherein a spatial position of the adjustable pivot assembly is selected by adjustment of the support bar connector at its point of fixation to the fixed frame portion, the adjustment including rotational motion around each one of three axis that are normal to each other and that transect the rigid support bar and adjustable connector, and translational motion along at least two of each of the three axis that are normal to each other and that transect the rigid support bar and adjustable connector the surgical tool comprising an attachment feature for releasable fixation to one or more of the support bar and the adjustable pivot assembly wherein adjustment and locking of the support bar connector effectively fixes in space the position of the adjustable pivot assembly, and thereby fixes the point of attachment of the surgical tool.

17. A surgical instrument assembly, comprising:

(a) a surgical table having first and second ends and a surface suitable to support a surgical subject in a prone or supine position with the surgical subject oriented along a superior to inferior axis of the surgical table between its first and its second ends;

(b) a rigid support bar that is affixed to a surgical instrument assembly, the rigid support bar having a surgical tool attachment feature wherein the rigid support bar is positionable above the surgical table, and wherein the surgical tool attachment feature of the rigid support bar is adjustably positionable at a point that is defined by an intersection of three axes that are normal to each other and that transect the surgical tool attachment feature, a first of the three axes being parallel to the superior to inferior axis of the surgical table, a second of the three axes being perpendicular to the superior to inferior axis of the surgical table and in a plane that extends in a lateral dimension that is transverse to the superior to inferior axis of the surgical table, and a third of the three axes being perpendicular to and transecting the superior to inferior axis of the surgical table (c) a modular surgical retractor comprising, a retractor body and a retractor hood, the retractor body and retractor hood each comprising a proximal end that is adapted to extend outside of the surgical field and a distal end that is adapted to extend into the surgical field, the retractor body and retractor hood engageable to form a through channel disposed between open proximal and distal ends that are defined by the proximal and distal ends of the retractor body and retractor hood, and bounded by the retractor body and retractor hood, the through channel having a central channel axis, the retractor body comprising a floor extending along a retractor body longitudinal axis, and the retractor hood comprising a body extending along a retractor hood longitudinal axis, each of the retractor body and retractor hood being independently operable to manipulate soft tissue and adapted to be adjustably and releasably coupled at their proximal ends with general alignment of their respective longitudinal axes, the retractor body and the retractor hood each comprising at its proximal end a coupling element for adjustably and releasably coupling the retractor body and retractor hood, one of the coupling elements comprising one or a plurality of fasteners, and the other of the coupling elements comprising one or a plurality of receivers, wherein when uncoupled, the retractor hood can be aligned with the retractor body and at least partially compressed against the retractor body, and wherein, when coupled, the retractor body and retractor hood are displaced from one another vertically and constrained to one or more of three degrees of freedom, being movable pivotally around a pivot axis at the proximal end that is perpendicular to the channel longitudinal axis, displaceable vertically from between a compressed orientation up to a pre selected displacement distance, or slidable horizontally along the channel longitudinal axis, or combinations of these.

18. The surgical instrument assembly according to claim 17, wherein the modular surgical retractor comprises one or more of the features selected from the group consisting of:

the retractor body is substantially curvilinear along its longitudinal axis and has a radius of curvature from 5 to 50 cm;

the distal end of one or both the retractor body and retractor hood is contoured and wherein the contour describes a concave arc that transects the retractor's longitudinal axis and has a radius of curvature from 0.5 cm to 10 cm, and wherein the contour is bounded by bosses;

the retractor hood is rectilinear along its longitudinal axis, and is either rectilinear or bowed around its longitudinal axis along at least a portion of its length;

the retractor body comprises two opposing sidewalls bounding the floor along at least part of the length of the floor, the floor and sidewalls extending along the longitudinal axis and defining a chute with an open top, wherein the retractor body sidewalls are selected from essentially planar and bowed; and, at least one of the retractor and the hood comprises at least one tissue fixation member, comprising: a retractor securement element and a tissue securement element, the retractor securement element securable to one or both of the retractor body and retractor hood, and the tissue securement element is securable to a target tissue in the surgical field and selected from a screw, a pin, a wire, an awl, and a tang.

19. A surgical instrument assembly, comprising:
(a) a surgical table having first and second ends and a surface suitable to support a surgical subject with the surgical subject oriented along a superior to inferior axis of the surgical table between its first and its second ends;
(b) a rigid support bar that is affixed at a first end to an adjustable pivot assembly comprising a spherical head affixed, and a socket member engagable with the spherical head and adapted for fixation to a surgical tool, wherein the adjustable pivot assembly affixed to the rigid support bar is positionable above the surgical table, and wherein the surgical tool, when engaged with the adjustable pivot assembly, is adjustably positionable at a point that is defined by an intersection of three axes that are normal to each other and that transect the surgical tool, a first of the three axes being parallel to the superior to inferior axis of the surgical table, a second of the three axes being perpendicular to the superior to inferior axis of the surgical table and in a plane that extends in a lateral dimension that is transverse to the superior to inferior axis of the surgical table, and a third of the three axes being perpendicular to and transecting the superior to inferior axis of the surgical table.

20. The surgical instrument assembly according to claim 19, wherein the rigid cross bar is adapted at a second end for fixed attachment to the surgical table.

* * * * *

UNITED STATES PATENT AND TRADEMARK OFFICE
CERTIFICATE OF CORRECTION

| | |
|---|---|
| PATENT NO. | : 10,687,830 B2 |
| APPLICATION NO. | : 15/747935 |
| DATED | : June 23, 2020 |
| INVENTOR(S) | : Javier Garcia-Bengochea, Marc Von Amsberg and Ryan Lewis |

It is certified that error appears in the above-identified patent and that said Letters Patent is hereby corrected as shown below:

On the Title Page

Item (63) should be removed completely.

In the Specification

Column 1, Lines 12-22 should read:
PRIORITY CLAIMS; RELATED APPLICATIONS:
This application claims priority to and is a 35 USC 371 US National Stage Application of International Patent Application No. PCT/US2016/044119 that was filed on Jul. 26, 2016, which has a priority date of Jul. 26, 2015, and which claims priority to U.S. Provisional Applications Ser. No. 62/197,093 filed Jul. 26, 2015, and 62/246,566 filed Oct. 26, 2015, the entireties of which are incorporated herein by reference.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*